United States Patent [19]
Sykes et al.

[11] Patent Number: 5,658,564
[45] Date of Patent: Aug. 19, 1997

[54] XENOGRAFT THYMUS

[75] Inventors: Megan Sykes, Boston; David H. Sachs, Newton, both of Mass.

[73] Assignee: The General Hospital Corporation, Boston, Mass.

[21] Appl. No.: 243,653

[22] Filed: May 16, 1994

Related U.S. Application Data

[63] Continuation-in-part of Ser. No. 220,371, Mar. 29, 1994, abandoned, Ser. No. 212,228, Mar. 14, 1994, abandoned, PCT/US94/01616, Feb. 14, 1994, Ser. No. 150,739, Nov. 10, 1993, Ser. No. 126,122, Sep. 23, 1993, abandoned, Ser. No. 114,072, Aug. 30, 1993, Ser. No. 838,595, Feb. 19, 1992, abandoned, and Ser. No. 163,912, Dec. 7, 1993, abandoned, which is a continuation-in-part of Ser. No. 62,946, May 17, 1993, abandoned.

[51] Int. Cl.$^6$ .......................... A01N 63/00; A61K 35/26
[52] U.S. Cl. .................. 424/93.3; 424/93.7; 424/580
[58] Field of Search ............................................ 424/93.7

[56] References Cited

U.S. PATENT DOCUMENTS

| | | |
|---|---|---|
| 4,772,552 | 9/1988 | Hercend et al. ........................... 435/7 |
| 5,087,570 | 2/1992 | Weissman et al. .................. 435/240.1 |
| 5,160,490 | 11/1992 | Naughton et al. ...................... 435/284 |

FOREIGN PATENT DOCUMENTS 0 341966  11/1989  European Pat. Off. .

OTHER PUBLICATIONS

08/150739 Nov. 10, 1993.
08/129608 Sep. 29, 1993.
08/126122 Sep. 23, 1993.
08/114072 Aug. 30, 1993.
Aksentijeivch, I., et al., "Natural Antibodies Can Inhibit Bone Marrow Engraftment In the Rat→Mouse Species Combination", *J. Immunology* 147:4140–4146 (1991).
Anklesaria, P., et al., "Engraftment Of A Clonal Bone Marrow Stromal Cell Line In Vivo Stimulates Hematopoietic Recovery From Total Body Irradiation", *Proc. Natl. Acad. Sci. USA* 84:7681–7685 (1987).
Auchincloss, Federal Research in Progress, I.D. No.: 5RO1HL36372–05.
Ba, D., et al., "Restoration Of T Cell Depression And Suppression Of Blood Pressure In Spontaneously Hypertensive Rats (SHR) By Thymus Grafts or Thymus Extracts", *J. Immunology* 128:1211–1216 (1982).
Ba, D., et al. "Restoration Of Immune Functions And Subsequent Suppression Of Blood Pressure In Spontaneously Hypertensive Rats By Allogeneic, Xenogeneic Thymus Grafts Or Injection Of Thymus Extracts", *Chinese Med. J.* 94(6):369–374 (1981).
Barber, W. Henry, et al., "Long–Term Results Of A Controlled Prospective Study With Transfusion Of Donor–Specific Bone Marrow In 57 Cadaveric Renal Allograft Recipients", *Transplantation* 51:070–075 (Jan., 1991).
Belo, et al., Int. Immunol., 1:105, 1989.
Billingham, R.E., et al., "Actively Acquired Tolerance Of Foreign Cells", *Nature* 172:603–606 (Jul. 4, 1953 to Dec. 26, 1953).
Bix, M., et al., "Inefficient Positive Selection Of T Cells Directed By Haematopoietic Cells", *Nature* 359:330–333 (1992).
Buckley, R.H., et al., "Correction Of Severe Combined Immunodeficiency By Fetal Liver Cells", *N.E. J. Med.* 194:1076–1081 (1976).
Campos, L., et al., "Prolonged Survival Of Rat Orthotopic Liver Allografts After Intrathymic Inoculation Of Donor–Strain Cells", *Transplantation* 54(4):866–869 (1993).
Cosimi, A. B., et al., "Experience With Large–Dose Intravenous Antithymocyte Globulin In Primates And Man", *Surgery* 68(1):54–61 (1970).
Cooper, D.K.C., et al., "Effects of Cyclosporine And Antibody Adsorption On Pig Cardiac Xenograft Survival In The Baboon", *J. Heart Transplant.* 7(3):238–246 (1988).
Dalmassio, *Federal Research in Progress*, I.D. No.: 0003; 73094; 618 "Inhibition of complement activation in xenotransplantation".
Deugnier, M., et al., "Rat bone marrow cells undergo thymopoiesis in mouse fetal thymic organ culture", *Eur. J. Immunol.* 20:2075–2081 (1990).
El–Ezz, A.Y., et al., "T–Cell Development In Thymectomized Fully Xenogeneic Chimeras (Rat→Mouse): Evidence For Extrathymic T–Cell Maturation", *FASB J* 6(5):A1697 (1992).
El Ezz, A.Y., et al., "Mixed Xenogeneic Chimeras (Mouse+ Rat→Mouse): The Mouse Thymus Is Sufficient To Support Xenogeneic Rat T–Cell Maturation", *J. Cell. Biochem. Supp. O.* (16 part A):181 (1992).
Fiedler, et al., "Experimental xenografting in widely divergent species, modification of the hyperacute xenogeneic rejection of kidneys from pigs (donor) by extreme hemodilution of dogs" 163:137–153, 1974.
Fischel R.J., et al., "Prolonged Survival of a Discordant Cardiac Xenograft in a Rhesus Monkey", *Transplantation Proc.* 23(1):589–590 (1991).
Fischel, R.J., et al., "Removal of IgM Anti–Endothelial Antibodies Results in Prolonged Cardiac Xenograft Survival", *Transplantation Proc.* 23(3):1077–1078 (1990).
Gao, E., et al., "Strong T Cell Tolerance In Parent→$F_1$ Bone Marrow Chimeras Prepared With Supralethal Irradiation", *J. Exp. Med.* 171:1101–1121 (1990).
Guillemot, F.P., et al., "Cells Expressing Ia Antigens In The Avian Thymus", *J. Exp. Med.* 160:1803–1819 (1984).Gustafsson, K., et al., "Structure of miniature swine class II DRB genes: Conservation of hypervariable amino acid residues between distantly related mammalian species", *Proc. Natl. Acad. Soc. USA* 87:9798–9802 (1990).

(List continued on next page.)

*Primary Examiner*—Suzanne E. Ziska
*Attorney, Agent, or Firm*—Louis Myers; Lahive & Cockfield

[57] ABSTRACT

The invention features methods of replacing thymus function and inducing immunological tolerance.

24 Claims, 3 Drawing Sheets

OTHER PUBLICATIONS

Guzzetta, P., et al., "Induction Of Kidney Transplantation Tolerance Across Major Histocompatibility Complex Barriers By Bone Marrow Transplantation In Miniature Swine", *Transplantation* 51(4):862–866 (1991).

Hallenbeck, G.A., et al., "Restoration of Immunologic Competence of Neonatally Thymectomized Mice by Isogeneic and Xenogeneic Thymic Grafts", *Proc. Soc. Exp. Biol. Med.* 130(4):1142–1146 (1969).

Hougen, H.P., et al., "The thymus reconstituted nude rat: Lymphocyte subpopulations and immunological characteristics", *Thymus* 10:207–217 (1987).

Hammer, C., et al., "Preformed Natural Antibodies in Animals and Man", *Europ. Surg. Res.* 5:162–166 (1973).

Hougen, H.P., et al., "Effects of xenogeneic, allogeneic and isogeneic thymus grafts on lymphocyte populations in peripheral lymphoid organs of the nude rat", *Laboratory Animals* 21:103–111 (1987).

Ildstad, S.T., et al., "Cross–species Bone Marrow Transplantation: Evidence for Tolerance Induction, Stem Cell Engraftment, and Maturation of T Lymphocytes in a Xenogeneic Stromal Environment (Rat→Mouse)", *J. Exp. Med.* 174:467–478 (1991).

Ildstad, S.T., et al., "Reconstitution with xyngeneic plus allogeneic or xenogeneic bone marrow leads to specific acceptance of allografts or xenografts", *Nature* 307:168–170 (1984).

Irwin, M.J., et al., "Species–Restricted Interactions Between CD8 And the $\alpha 3$ Domain Of Class I Influence The Magnitude Of The Xenogeneic Response", *J. Exp. Med.* 170:1091–1101 (1989).

Jotereau, F.V., et al., "Demonstration Of A Cyclic Renewal Of The Lymphocyte Precursor Cells In The Quail Thymus During Embryonic And Perinatal Life", *J. Immunol.* 129(5):1869–1877 (1982).

Jotereau, F.V., et al., "Lymphoid stem cell homing to the early thymic primordium of the avian embryo", *Euro. J. Immunol.* 10:620–627 (1980).

Kollmann, T.R., et al., "The Concurrent Maturation of Mouse and Human Thymocytes in Human Fetal Thymus Implanted in NIH–beige–nude–xid Mice is Associated with the Reconstitution of the Murine Immune System", *J. Exp. Med.* 177:821–832 (1993).

Kosaka, H., et al., "Tolerance of CD8+ T Cells Developing in Parent→$F_1$ Chimeras Prepared with Supralethal Irradiation: Step–Wise Induction of Tolerance in the Intrathymic and Extrathymic Environments", *J. Exp. Med.* 177:367–378 (1993).

Krowka, J.F., et al., "Human T Cells In The SCID–hu Mouse Are Phenotypically Normal And Functionally Competent", *J. Immunol.* 146(11):3751–3756 (1991).

Latinne, D., et al., "Xenotransplantation From Pig to Cynomolgus Monkey: Approach Toward Tolerant Induction", *Transplantation Proc.* 25(1):336–338 (1993).

Lawrance, S.K., et al., "Transgenic HLA–DR$\alpha$ Faithfully Reconstitutes IE–Controlled Immune Functions and Induces Cross–Tolerance to E$\alpha$ in E$\alpha^0$ Mutant Mice", *Cell* 56:583–594 (1989).

Le Douarin, N.M., et al., "Ontogeny of Primary Lymphoid Organs and Lymphoid Stem Cells", *Am. J. Anat.* 170:261–299 (1984).

Le Douarin, N.M., et al., "Distribution and Origin of Ia–Positive Cells in the Avian Thymus Analyzed by Means of Monoclonal Antibodies in Heterospecific Chimeras", *Prog. Immunol. V.* pp. 613–631 (1983).

Le Douarin, N.M., et al., "Demonstration Of A Cyclic Renewal Of The Lymphocyte Precursor Cells In the Quail Thymus During Embryonic And Perinatal Life" *J. Immunol.* 129:1869 (1982).

Le Douarin, N.M., et al., "Tracing Of Cells Of The Avian Thymus Through Embryonic Life In Interspecific Chimeras", *J. Exp. Med.* 142:17–40 (1975).

Lee, L.A., "Murine T Cell Maturation In Discordant Xenogeneic Fetal Thymus Grafts", *J. Immunol.* 150(8 part 2):321A (1993).

Lubin, I., et al., "Engraftment and Development of Human T and B Cells in Mice After Bone Marrow Transplantation", *Science* 252:427–431 (1991).

Lucas, P.J., et al., "The Human Antimurine Xenogeneic Cytotoxic Response", *J. Immunol.* 144(12):4548–4554 (1990).

Manning, J.K., et al., "Transplantation of Cultured Thymic Fragments: Results in Nude Mice", *Scand. J. Immunol.* 19:403–410 (1984).

Manning, J.K., et al., "Effect Of Transplantation Of Xenogeneic Cultured Thymic Fragments (CTF) in Nude Mice," *Federation Proceedings* 41(3):605 (1982).

Markmann, J.F., et al., "Deletion Of Donor–Reactive T Lymphocytes In Adult Mice After Intrathymic Inoculation With Lymphoid Cells", *Transplantation* 55(4):871–877 (1993).

Mayumi, H., et al., "Long–Lasting Skin Allograft Tolerance In Adult Mice Induced Across Fully Allogeneic (Multimajor H–2 Plus Multiminor Histocompatibility) Antigen Barriers By A Tolerance–Inducing Method Using Cyclophosphamide", *J. Exp. Med.* 169:213–238 (1989).

McCune, J.M., et al., "The SCID–hu Mouse: Murine Model for the Analysis of Human Hematolymphoid Differentiation and Function", *Science* 241:1632–1639 (1988).

McDuffie, M., et al., "Involvement Of Major Histocompatibility Complex Products In Tolerance Induction in The Thymus", *J. Immunol.* 141(16):1840–1847 (1988).

Miyake, K., et al., "Evidence for a Role of the Integrin VLA–4 in Lympho–hemopoiesis", *J. Exp. Med.* 173:599–607 (1991).

Myburgh, J.A., et al., "Total Lymphoid Irradiation in Kidney And Liver Transplantation In The Baboon: Prolonged Graft Survival And Alterations In T Cell Subsets With Low Cumulative Dose Regimens", *J. Immunol.* 132(2):1019–1025 (1984).

Nakafusa, Y., et al., "Induction Of Donor–Specific Tolerance To Cardiac But Not Skin Or Renal Allografts By Intrarhythmic Injection Of Splenocyte Alloantigen", *Transplantation* 55(4):877–882 (1993).

Namikawa, R., et al., "Long–Term Human Hematopoiesis in the SCID–hu Mouse", *J. Exp. Med.* 172:1055–1063 (1990).

Ohki, H., et al., "Tolerance Induced by Thymic Epithelial Grafts in Birds", *Science* 237:1032–1035 (1989).

O'Reilly, R.J., et al., "Transplantation of Marrow–Depleted T Cells by Soybean Lectin Agglutination and E–Rosette Depletion: Major Histocompatibility Complex–Related Graft resistance in Leukemic Transplant Recipients", *Transplantation Proc.* XVII(1):455–459 (1985).

Pennington, L.R., et al., "Bone Marrow Transplantation in Miniature Swine", *Transplantation* 45(1):21–26 (1988).

Pescovitz, et al., "Effect of Class II Antigen Matching on Renal Allograft Survival in Miniature Swine", *J. Exp. Med.* 160:1495–1508 (1984).

Platt, J.L., et al., "Immunopathology Of Hyperacute Xenograft Rejection In A Swine–To–Primate Model", *Transplantation* 52(2):214–220 (1991).

Platt, J.L., et al., "Natural Antibody And The Classical Complement Pathway Mediate Hyperacute Xenograft Rejection In Pig To Primate Combinations", *FASEB, 75th Annual Meeting Abstracts* 7761:A1707 (1990).

Platt, J.L., et al., "An Elisa Assay For Xenoreactive Natural Antibodies", *Transplantation* 49(5):1000–1001 (1990).

Platt, J.L., et al., "Transplantation of discordant xenografts: a review of progress", *Immunol. Today* 11:451–456 (1990).

Pratt, K., et al., "Molecular identification and characterization of B (β) genes from the SLA"haplotype", *Immunogenetics* 31:1–6 (1990).

Rayfield, L.S., et al., "Tolerance, Immunocompetence, And Secondary Disease In Fully Allogeneic Radiation Chimeras", *Transplantation* 36(2):183–189 (1983).

Rodt, et al., "Effect of heterologous anti–brain antibodies on acute secondary disease in mice", *Eur. J. Immunol.* 4:25–29 (1975).

Sachs, D.H., et al., "Class II gene characterization by RFLP and by isolation form a genomic library", *Immunogenetics* 28:22–29 (1988).

Salaün, J., et al., "Thymic Epithelium Tolerizes for Histocompatibility Antigens", *Science* 247:1471–1474 (2990).

Schilling, A., et al., "Experimental xenografting in widely divergent species: Interaction of humoral factors in hyperacute xenograft rejection in the rat–dog system", *Res. Exp. Med.* 165:79–92 (1975).

Schönbeck, S., et al., "Transplantation of Thymic Autoimmune Microenvironment to Severe Combined Immunodeficiency Mice", *J. Clin. Invest.* 90:245–250 (1992).

Sharabi, Y., et al., "Specific Tolerance Induction Across A Xenogeneic Barrier: Production of Mixed Rat/Mouse Lymphohematopoietic Chimeras Using a Nonlethal Preparative Regimen", *J. Exp. Med.* 172:195–202 (1990).

Slapak, M., et al., "Effect of Heparin, Arvin, Liver Perfusion, and Heterologous Antiplatelet Serum on Rejection of Pig Kidney by Dog", *Transplantation Proc.* III(I):558–561 (1971).

Soderling, C.C.B., et al., "A Correlation Between Conditioning And Engraftment In Recipients of MHC–Mismatched T Cell–Depleted Murine Bone Marrow Transplants", *J. Immunol.* 135:941–946 (1985).

Speiser, D.E., et al., "Clonal Deletion Induced by Either Radioresistant Thymic Host Cells or Lymphohemopoietic Donor Cells at Different Stages of Class I–restricted T Cell Ontogeny", *J. Exp. Med.* 175:1277–1283 (1992).

Sykes, M., et al., "Bone marrow transplantation as a means of inducing tolerance", *Seminars in Immunol.* 2:401–417 (1990).

Sykes, M., et al., "Mixed allogeneic chimerism as an approach to transplantation tolerance", *Immunol. Today* 9:23–27 (1988).

Taguchi, O., et al., "Development Of Multiple Organ–Localized Autoimmune Diseases In Nude Mice After Reconstitution Of T Cell Function By Rat Fetal Thymus Graft", *J. Exp. Med.* 164:60–71 (1986).

Takeuchi, M., et al., "Rat Thymic Epithelium Positively Selects Mouse T Cells with Specificity for Rat MHC Class II Antigens but Fails to Induce Detectable Tolerance in the Mouse T Cells to the Rat MHC Antigens", *Immunobiol.* 186:421–434 (1992).

Thomas, J.M., et al., "Veto Cells Induce Long–Term Kidney Allograft Tolerance in Primates Without Chronic Immunosuppression", *Transplantation Proc.* 23(1):11–13 (1991).

Thomas, J.M., et al., "Promotion Of Incompatible Allograft Acceptance In Rhesus Monkeys Given Posttransplant Antithymocyte Globulin And Donor Bone Marrow", *Transplantation* 47(2):209–215 (1989).

Trager, D.K., et al., "Cardiac Allograft Prolongation In Mice Treated With Combined Posttransplantation Total–Lymphoid Irradiation And Anti–L3T4 Antibody Therapy", *Transplantation* 47(4):587–591 (1989).

Waldmann, H., "Manipulation Of T–Cell Responses With Monoclonal Antibodies", *Ann. Rev. Immunol.* 7:407–444 (1989).

Wee, S.L., et al., "The Effects Of OKT4A Monoclonal Antibody On Cellular Immunity Of Nonhuman Primate Renal Allograft Recipients", *Transplantation* 53(3):501–507 (1992).

Williams, D.A., et al., "Fibronectin and VLA–4 in haematopoietic stem cell–microenvironment interactions", *Nature* 352:438–441 (1991).

Wren, S.M., et al., "Kinetics of early T–cell repopulation in fully xenogeneic chimeras (F344 rat→B10 mouse): Evidence for rat T–cell maturation in a xenogeneic mouse thymus", *Surgery* 110(2):238–246 (1991).

Martin et al., "Successful xenogeneic transplantation in embryos: induction of tolerance by extrathymic chick tissue grafted into quail", Dev. Immunology, 1:265–277, 1991.

Salaw et al Science 247: 1471, 1990.

Sharah et al Jeol 172: 195, 1990.

Cooper et al J Heart Transplantation.

Knuhn et al J f Immunol 146(11): 3751, 1991.

Dalmarso et al Am. J. Pathol 140(5): 1157, 1992.

Bonomo et al., "Thymus epithelium induces tissue–specific tolerance" J. Exp. Med. 177:1153, 1993.

Ramsdell et al., "A nondeletional mechanism of thymic self tolerance" Science 246:1038, 1989.

XENOGRAFT THYMUS

BACKGROUND OF THE INVENTION

This application is a continuation-in-part of Sykes, U.S. Ser. No. 08/163,912, filed Dec. 7, 1993, now abandoned which is a continuation in part of Sykes U.S. Ser. No. 08/062,946, filed on May 17, 1993, now abandoned. This application is also a continuation-in-part of: U.S. Ser. No. 08/220,371, filed Mar. 29, 1994, now abandoned; U.S. Ser. No. 08/212,228, filed Mar. 14, 1994, now abandoned; U.S. Ser. No. 08/150,739, filed Nov. 10, 1993; U.S. Ser. No. 08/126,122, filed on Sep. 23, 1993, now abandoned; U.S. Ser. No. 08/114,072, filed Aug. 30, 1993; U.S. Ser. No. 07/838,595, filed Feb. 19, 1992, now abandoned; and PCT/US94/01616 filed Feb. 14, 1994. All of the above-recited U.S. patent application and International Applications are hereby incorporated by reference.

This invention relates to the replacement of thymus function and to the induction or restoration of immunological tolerance.

The thymus is the central organ for the development of mature, self-tolerant T cells that recognize peptide antigens in the context of self major histocompatibility (MHC) antigens. The requirement for self MHC molecules to present antigen is termed MHC restriction. Athymic individuals do not have an organ in which to generate normal numbers of MHC restricted T cells and are therefore immunoincompetent.

SUMMARY OF THE INVENTION

It has been discovered that host T cells of an athymic T cell depleted host which has received a thymic graft, e.g., a xenogeneic thymic gaff, can mature in the donor thymic tissue, e.g., in xenogeneic thymic tissue. Host T cells which mature in the implanted xenogeneic thymic tissue are immunoincompetent.

Accordingly, the invention features, in one aspect, a method of restoring or inducing immunocompetence (or restoring or promoting the thymus-dependent ability for T cell progenitors to mature or develop into functional mature T cells) in a host or recipient, e.g., a primate host or recipient, e.g., a human, which is capable of producing T cell progenitors but which is thymus-function deficient and thus unable to produce a sufficient number of mature functional T cells for a normal immune response. The invention includes the steps of introducing into the primate host, donor thymic tissue, e.g., xenogeneic thymic tissue, preferably fetal or neonatal thymic tissue, so that host T cells can mature in the implanted thymic tissue.

In preferred embodiments the donor of the thymic tissue is a xenogeneic species and: the thymic xenograft is a discordant xenograft; the thymic xenograft is a concordant xenograft; the host is a primate, e.g., a human, and the thymic tissue is swine, e.g., miniature swine, thymic tissue, or primate thymic tissue.

The method can include other steps which facilitate acceptance of the donor tissue, or otherwise optimize the method. In preferred embodiments the thymic tissue is xenogeneic and: liver or spleen tissue, preferably fetal or neonatal liver or spleen tissue, is implanted with the thymic tissue; donor hemopoietic cells, e.g., cord blood stem cells or fetal or neonatal liver or spleen cells, are administered to the recipient, e.g., a suspension of fetal liver cells is administered intraperitoneally or intravenously; the recipient is thymectomized, preferably before or at the time the xenograft thymic tissue is introduced.

In other preferred embodiments the method includes: (preferably prior to or at the time of introducing the thymic tissue into the recipient) depleting, inactivating or inhibiting recipient natural killer (NK) cells, e.g., by introducing into the recipient an antibody capable of binding to NK cells of the recipient, to prevent NK mediated rejection of the thymic tissue; (preferably prior to or at the time of introducing the thymic tissue into the recipient) depleting, inactivating or inhibiting host T cell function, e.g., by introducing into the recipient an antibody capable of binding to T cells of the recipient; (preferably prior to or at the time of introducing the thymic tissue into the recipient) depleting, inactivating or inhibiting host $CD4^+$ cell function, e.g., by introducing into the recipient an antibody capable of binding to CD4, or $CD4^+$ cells of the recipient.

Other preferred embodiments include the step of (preferably prior to thymic tissue or hematopoietic stem cell transplantation) creating hematopoietic space, e.g., by one or more of: irradiating the recipient mammal with low dose, e.g., between about 100 and 400 rads, whole body irradiation, the administration of a myelosuppressive drug, or the administration of a hematopoietic stem cell inactivating or depleting antibody, to deplete or partially deplete the bone marrow of the recipient (preferably prior to thymic tissue transplantation).

Other preferred embodiments include (preferably prior to thymic tissue or hematopoietic stem cell transplantation) inactivating thymic T cells by one or more of: irradiating the host with, e.g., about 700 rads of thymic irradiation, administering to the recipient one or more doses of an anti T cell antibody, e.g., an anti-CD4 and/or an anti-CD8 monoclonal antibody, or administering to the recipient a short course of an immunosuppressant, as is described in U.S. Ser. No. 08/220,371.

Other preferred embodiments include depleting or otherwise inactivating natural antibodies, e.g., by one or more of: the administration of a drag which depletes or inactivates natural antibodies, e.g., deoxyspergualin; the administration of an anti-IgM antibodies; or the absorption of natural antibodies from the host's blood, e.g., by contacting the host's blood with donor antigen, e.g., by hemoperfusion of a donor organ, e.g., a kidney or a liver, from the donor species.

In preferred embodiments the host or recipient is a post-natal individual, e.g., an adult, or a child.

In preferred embodiments the method further includes the step of identifying a host or recipient which is capable of producing T cell progenitors but which is thymus-function deficient and thus unable to produce a sufficient number of mature functional T cells for a normal immune response.

In other preferred embodiments, a graft which is obtained from a different organ than is the thymic tissue is implanted in the recipient; and the recipient does not receive hematopoietic stem cells, e.g., bone marrow cells, from the donor or the donor species.

Other methods can be combined with the methods disclosed herein to promote the acceptance of the graft by the recipient. For example, tolerance to the donor tissue can also be induced by inserting a nucleic acid which expresses a donor antigen, e.g., a donor MHC gene, into a cell of the recipient, e.g., a hematopoietic stem cell, and introducing the genetically engineered cell into the recipient. For example, human recipient stem cells can be engineered to express a swine MHC gene, e.g., a swine class I or class II MHC gene, or both a class I and a class II gene, and the cells implanted in a human recipient who will receive swine thymic tissue. When inserted into a recipient primate, e.g., a human, expression of the donor MHC gene results in tolerance to subsequent exposure to donor antigen, and can thus induce tolerance to thymic tissue from the donor. These methods, and other methods which can be combined with the methods disclosed herein, are discussed in Sachs, U.S. Ser. No. 08/126,122, filed Sep. 23, 1993, hereby incorporated by reference and in Sachs, U.S. Ser. No. 08/129,608, filed Sep. 29, 1993, hereby incorporated by reference.

Methods of inducing tolerance, e.g., by the implantation of hematopoietic stem cells, disclosed in Sachs, Cosimi, and Sykes, U.S. Ser. No. 07/838,595, filed Feb. 19, 1992, hereby incorporated by reference, can also be combined with the methods disclosed herein.

Other methods of inducing tolerance may also be used to promote acceptance of the donor tissue. For example, suppression of T cell help, which can be induced, e.g., by the administration of a short course of high dose immunosuppresant, e.g., cyclosporine, has been found to induce tolerance. In these methods, T cell help is suppressed for a comparatively short period just subsequent to implantation of a graft, and does not require or include chronic immunosuppression. These methods, as well as other methods which can be combined with the methods disclosed herein, are described in Sachs, U.S. Ser. No. 08/220,371, filed Mar. 29, 1994, hereby incorporated by reference.

Other methods of promoting tolerance or promoting the acceptance of grafts, e.g., by altering levels of cytokine activity, are disclosed in Sachs, LeGuern, Sykes, and Blancho, U.S. Ser. No. 08/114,072; filed Aug. 30, 1993, hereby incorporated by reference.

It has also been discovered that xenogeneic thymic tissue can be used to induce tolerance to a xenogeneic graft in a recipient.

Accordingly, in another aspect, the invention features, a method of inducing tolerance in a recipient mammal, e.g., a primate, e.g., a human, of a first species to a graft obtained from a mammal of a second species, e.g., a discordant species. The method includes: prior to or simultaneous with transplantation of the graft, introducing into the recipient mammal thymic tissue, e.g., thymic epithelium, preferably fetal or neonatal thymic tissue, of the second species; and (optionally) implanting the graft in the recipient. The thymic tissue prepares the recipient for the graft that follows, by inducing immunological tolerance at the T-cell level.

In preferred embodiments: the thymic xenograft is a discordant xenograft; the thymic xenograft is a concordant xenograft; the recipient is a human and the thymic tissue is swine, e.g., miniature swine, thymic tissue, or primate thymic tissue.

Preferred embodiments include other steps to promote acceptance of the graft thymus and the induction of immunological tolerance or to otherwise optimize the procedure. In preferred embodiments: liver or spleen tissue, preferably fetal or neonatal liver or spleen tissue, is implanted with the thymic tissue; donor hemopoietic cells, e.g., cord blood stem cells or fetal or neonatal liver or spleen cells, are administered to the recipient, e.g., a suspension of fetal liver cells administered intraperitoneally or intravenously; the recipient is thymectomized, preferably before or at the time the xenograft thymic tissue is introduced.

In other preferred embodiments the method includes (preferably prior to or at the time of introducing the thymic tissue or stem cells into the recipient) depleting, inactivating or inhibiting recipient NK cells, e.g., by introducing into the recipient an antibody capable of binding to natural killer (NK) cells of the recipient, to prevent NK mediated rejection of the thymic tissue; (preferably prior to or at the time of introducing the thymic tissue into the recipient) depleting, inactivating or inhibiting recipient T cells, e.g., by introducing into the recipient an antibody capable of binding to T cells of the recipient; (preferably prior to or at the time of introducing the thymic tissue or stem cells into the recipient) depleting, inactivating or inhibiting host $CD4^+$ cell function, e.g., by introducing into the recipient an antibody capable of binding to CD4, or $CD4^+$ cells of the recipient. An anti-mature T cell antibody which lyses T cells as well as NK cells can be administered. Lysing T cells is advantageous for both thymic tissue and xenograft survival. Anti-T cell antibodies are present, along with anti-NK antibodies, in anti-thymocyte anti-serum. Repeated doses of anti-NK or anti-T cell antibody may be preferable. Monoclonal preparations can be used in the methods of the invention.

Other preferred embodiments include those in which: the recipient does not receive hemopoietic cells from the donor or the donor species: the same mammal of the second species is the donor of both the graft and the thymic tissue; the donor mammal is a swine, e.g., a miniature swine; an anti-human thymocyte polyclonal anti-serum, obtained, e.g., from a horse or pig is administered to the recipient.

Other preferred embodiments include the step of (preferably prior to thymic tissue or hematopoietic stem cell transplantation) creating hematopoietic space, e.g., by one or more of: irradiating the recipient mammal with low dose, e.g., between about 100 and 400 rads, whole body irradiation, the administration of a myelosuppressive drug, the administration of a hematopoietic stem cell inactivating or depleting antibody, to deplete or partially deplete the bone marrow of the recipient.

Other preferred embodiments include (preferably prior to thymic tissue or hematopoietic stem cell transplantation) inactivating thymic T cells by one or more of: irradiating the recipient with, e.g., about 700 rads of thymic irradiation, administering to the recipient one or more doses of an anti T cell antibody, e.g., an anti-CD4 and/or an anti-CD8 monoclonal antibody, or administering to the recipient a short course of an immunosuppressant, as is described in U.S. Ser. No. 08/220,371.

In preferred embodiments the host or recipient is a post-natal individual, e.g., an adult, or a child.

In preferred embodiments the method further includes the step of identifying a host or recipient which is in need of a graft.

Other preferred embodiments include depleting or otherwise inactivating natural antibodies, e.g., by one or more of: the administration of a drug which depletes or inactivates natural antibodies, e.g., deoxyspergualin; the administration of an anti-IgM antibodies; or the absorption of natural antibodies from the recipient's blood, e.g., by contacting the hosts blood with donor antigen, e.g., by hemoperfusion of a donor organ, e.g., a kidney or a liver, from the donor species.

Other methods can be combined with the methods disclosed herein to promote the acceptance of the graft by the recipient. For example, tolerance to the xenogeneic thymic tissue can also be induced by inserting a nucleic acid which expresses a donor antigen, e.g., a donor MHC gene, into a cell of the recipient, e.g., a hematopoietic stem cell, and introducing the genetically engineered cell into the recipient. For example, human recipient stem cells can be engineered to express a swine MHC gene, e.g., a swine class I or class II MHC gene, or both a class I and class II gene, and the cells implanted in a human recipient who will receive swine thymic tissue. When inserted into a recipient primate, e.g., a human, expression of the donor MHC gene results in tolerance to subsequent exposure to donor antigen, and can thus induce tolerance to thymic tissue from the donor. These methods, and other methods which can be combined with the methods disclosed herein, are discussed in Sachs, U.S. Ser. No. 08/126,122, filed Sep. 23, 1993, and in Sachs, U.S. Ser. No. 08/129,608, filed Sep. 29, 1993.

Methods of inducing tolerance, e.g., by the implantation of hematopoietic stem cells, disclosed in Sachs, Cosimi, and Sykes, U.S. Ser. No. 07/838,595, filed Feb. 19, 1992, can also be combined with the methods disclosed herein.

Other methods of inducing tolerance may also be used to promote acceptance of the xenogeneic thymic tissue. For example, suppression of T cell help, which can be induced, e.g., by the administration of a short course of high dose immunosuppresant, e.g., cyclosporine, has been found to induce tolerance. In these methods, T cell help is suppressed for a comparatively short period just subsequent to implantation of a graft, and does not require or include chronic immunosuppression. These methods, as well as other methods which can be combined with the methods disclosed herein, are described in Sachs, U.S. Ser. No. 08/220,371, filed Mar. 29, 1994.

Other methods of promoting tolerance or promoting the acceptance of grafts, e.g., by altering levels of cytokine activity, are disclosed in Sachs, LeGuern, Sykes, and Blancho, U.S. Ser. No. 08/114,072 filed Aug. 30, 1993.

In another aspect, the invention features, a method of restoring or inducing immunocompetence in a recipient, e.g., a primate recipient, e.g., a human, at risk for an acquired immune disorder, (e.g., a human at risk for AIDS), which is capable of producing T cell progenitors but which is thymus-function deficient and thus unable to produce a sufficient number of mature functional T cells to provide a normal immune response. The invention includes the steps of introducing into the primate recipient, donor thymic tissue, e.g., xenogeneic thymic tissue, so that recipient T cells can mature in the implanted donor thymic tissue. The thymic tissue is preferably fetal or neonatal thymic tissue.

In preferred embodiments the thymic tissue is xenogeneic and: the thymic xenograft is a discordant xenograft; the thymic xenograft is a concordant xenograft; the recipient is a human and the thymic tissue is vertebrate, e.g., swine, e.g., miniature swine, thymic tissue, or primate thymic tissue.

Acceptance of a graft, especially a xenogeneic graft, will depend on the stage of the immune disorder. Generally, the more advanced the disorder the more compromised the recipient immune system and the easier it is to induce acceptance of donor thymic tissue. In some cases, the tolerizing effect of the graft itself will be sufficient to provide for acceptance of xenogeneic thymus. In other cases, additional measures will be needed. Thus, the method can include other steps which facilitate acceptance of the donor tissue or otherwise optimize the method.

In preferred embodiments: liver or spleen tissue, preferably fetal or neonatal liver or spleen tissue, is implanted with the thymic tissue; donor hemopoietic cells, e.g., cord blood stem cells or fetal or neonatal liver or spleen cells, are administered to the recipient, e.g., a suspension of fetal liver cells is administered intraperitoneally or intravenously; the recipient is thymectomized, preferably before or at the time the xenograft thymic tissue is introduced.

In preferred embodiments: the method includes (preferably prior to or at the time of introducing the thymic tissue into the recipient) depleting, inactivating or inhibiting recipient NK cells, e.g., by introducing into the recipient an antibody capable of binding to natural killer (NK) cells of the recipient, to prevent NK mediated rejection of the thymic tissue; the method includes (preferably prior to or at the time of introducing the thymic tissue into the recipient), depleting, inactivating or inhibiting recipient T cells, e.g., by introducing into the recipient an antibody capable of binding to T cells of the recipient;(preferably prior to or at the time of introducing the thymic tissue into the recipient) depleting, inactivating or inhibiting host $CD4^+$ cell function, e.g., by introducing into the recipient an antibody capable of binding to CD4, or $CD4^+$ cells of the recipient.

Other preferred embodiments include the step of (preferably prior to thymic tissue or hematopoietic stem cell transplantation) creating hematopoietic space, e.g., by one or more of: irradiating the recipient mammal with low dose, e.g., between about 100 and 400 rads, whole body irradiation, the administration of a myelosuppressive drug, the administration of a hematopoietic stem cell inactivating or depleting antibody, to deplete or partially deplete the bone marrow of the recipient.

Other preferred embodiments include (preferably prior to thymic tissue or hematopoietic stem cell transplantation) inactivating thymic T cells by one or more of: irradiating the recipient mammal with, e.g., about 700 rads of thymic irradiation, administering to the recipient one or more doses of an anti T cell antibody, e.g., an anti-CD4 and/or an anti-CD8 monoclonal antibody, or administering to the recipient a short course of an immunosuppressant, as is described in U.S. Ser. No. 08/220,371.

Other preferred embodiments include depleting or otherwise inactivating natural antibodies, e.g., by one or more of: the administration of a drug which depletes or inactivates natural antibodies, e.g., deoxyspergualin; the administration of an anti-IgM antibodies; or the absorption of natural antibodies from the recipient's blood, e.g., by contacting the hosts blood with donor antigen, e.g., by hemoperfusion of a donor organ, e.g., a kidney or a liver, from the donor species.

In preferred embodiments the host or recipient is a post-natal individual, e.g., an adult, or a child.

In preferred embodiments the method further includes the step of identifying a host or recipient which is at risk for an acquired immune disorder, (e.g., a human at risk for AIDS), which is capable of producing T cell progenitors but which is thymus-function deficient and thus unable to produce a sufficient number of mature functional T cells to provide a normal immune response.

Other methods can be combined with the methods disclosed herein to promote the acceptance of the thymic graft by the recipient. For example, tolerance to donor tissue can also be induced by inserting a nucleic acid which expresses a donor antigen, e.g., a donor MHC gene, into a cell of the recipient, e.g., a hematopoietic stem cell, and introducing the genetically engineered cell into the recipient. For example, human recipient stem cells can be engineered to express a swine MHC gene, e.g., a swine class I or class II MHC gene, or both a class I and a class II MHC gene, and the cells implanted in a human recipient who will receive swine thymic tissue. When inserted into a recipient primate, e.g., a human, expression of the donor MHC gene results in tolerance to subsequent exposure to donor antigen, and can thus induce tolerance to thymic tissue from the donor. These methods, and other methods which can be combined with the methods disclosed herein, are discussed in Sachs, U.S. Ser. No. 08/126, 122, filed Sep. 23, 1993, hereby incorporated by reference and in Sachs, U.S. Ser. No. 08/220,371, filed Mar. 29, 1994.

Methods of inducing tolerance, e.g., by the implantation of hematopoietic stem cells, disclosed in Sachs, Cosimi, and Sykes, U.S. Ser. No. 07/838,595, filed Feb. 19, 1992, can also be combined with the methods disclosed herein.

Other methods of inducing tolerance may also be used to promote acceptance of the donor thymic tissue. For example, suppression of T cell help, which can be induced e.g., by the administration of a short course of high dose immunosuppresant, e.g., cyclosporine, has been found to induce tolerance. In these methods, T cell help is suppressed for a comparatively short period just subsequent to implantation of a graft, and does not require or include chronic immunosuppression. These methods, as well as other methods which can be combined with the methods disclosed herein, are described in Sachs, U.S. Ser. No. 08/220,371, filed Mar. 29, 1994.

Other methods of promoting tolerance or promoting the acceptance of grafts, e.g., by altering levels of cytokine activity, are disclosed in Sachs, LeGuern, Sykes, and Blancho, U.S. Ser. No. 08/114,072, filed Aug. 30, 1993.

In another aspect, the invention features, a method of restoring or inducing immunocompetence in a recipient, e.g., a primate recipient, e.g., a human, at risk for an acquired immune disorder, (e.g., a human at risk for AIDS) which is unable to produce a normal or sufficient number of mature functional T cells to provide normal immune function. The invention includes the steps of introducing into the primate recipient, donor hematopoietic stem cells, so that donor T cells can mature in the recipient thymus.

In preferred embodiments the donor stem cells are from a xenogeneic donor and: the xenograft hematopoietic stem cells are from a discordant species; the hematopoietic stem cells are from a concordant species; the recipient is a human and the hematopoietic stem cells are vertebrate, e.g., swine, e.g., miniature swine, hematopoietic stem cells, or primate hemopoietic stem cells.

Acceptance of the donor cells will depend on the stage of the immune disorder. Generally, the more advanced the disorder the more compromised the recipient immune system and the easier it is to induce acceptance of donor, especially xenogeneic donor, tissue. In some cases, the tolerizing effect of the stem cells themselves will be sufficient to provide for acceptance. In other cases, additional measures will be needed. Thus, the method can include other steps which facilitate acceptance of the donor cells or otherwise optimize the method. In preferred embodiments: liver or spleen tissue, preferably fetal or neonatal liver or spleen tissue, is implanted with the donor hemopoietic cells, e.g., cord blood stem cells or fetal or neonatal liver or spleen cells, are administered to the recipient, e.g., a suspension of fetal liver cells is administered intraperitoneally or intravenously.

In preferred embodiments: the method includes, (preferably prior to or at the time of introducing the donor cells into the recipient) depleting, inactivating or inhibiting recipient NK cells, e.g., by introducing into the recipient an antibody capable of binding to natural killer (NK) cells of the recipient, to prevent NK mediated rejection of the thymic tissue; the method includes (preferably prior to or at the time of introducing the thymic tissue into the recipient), depleting, inactivating or inhibiting recipient T cells, e.g., by introducing into the recipient an antibody capable of binding to T cells of the recipient; (preferably prior to or at the time of introducing the thymic tissue into the recipient) depleting, inactivating or inhibiting host $CD4^+$ cell function, e.g., by introducing into the recipient antibody capable of binding to CD4, or $CD4^+$ cells of the recipient.

Other preferred embodiments include the step of (preferably prior to thymic tissue or hematopoietic stem cell transplantation) creating hematopoietic space, e.g., by one or more of: irradiating the recipient mammal with low dose, e.g., between about 100 and 400 rads, whole body irradiation, the administration of a myelosuppressive drug, the administration of a hematopoietic stem cell inactivating or depleting antibody, to deplete or partially deplete the bone marrow of the recipient.

Other preferred embodiments include (preferably prior to thymic tissue or hematopoietic stem cell transplantation) inactivating thymic T cells by one or more of: irradiating the recipient mammal with, e.g., about 700 rads of thymic irradiation, administering to the recipient one or more doses of an anti T cell antibody, e.g., an anti-CD4 and/or an anti-CD8 monoclonal antibody, or administering to the recipient a short course of an immunosuppressant, as is described in U.S. Ser. No. 08/220,371.

Other preferred embodiments include depleting or otherwise inactivating natural antibodies, e.g., by one or more of: the administration of a drug which depletes or inactivates natural antibodies, e.g., deoxyspergualin; the administration of an anti-IgM antibodies; or the absorption of natural antibodies from the recipient's blood, e.g., by contacting the hosts blood with donor antigen, e.g., by hemoperfusion of a donor organ, e.g., a kidney or a liver, from the donor species.

In preferred embodiments the host or recipient is a post-natal individual, e.g., an adult, or a child.

In preferred embodiments the method further includes the step of identifying a host or recipient which is at risk for an acquired immune disorder, (e.g., a human at risk for AIDS) and which is unable to produce a a normal or sufficient number of mature functional T cells to provide normal immune function..

Other methods can be combined with the methods disclosed herein to promote the acceptance of the transplanted stem cells by the recipient. For example, tolerance to donor tissue can be induced by inserting a nucleic acid which expresses a donor antigen, e.g., a donor MHC gene, into a cell of the recipient, e.g., a hematopoietic stem cell, and introducing the genetically engineered cell into the recipient. For example, human recipient stem cells can be engineered to express a swine MHC gene, e.g., a swine class I or class II MHC gene, or both a class I and a class II gene, and the cells implanted in a human recipient who will receive swine thymic tissue. When inserted into a recipient primate, e.g., a human, expression of the donor MHC gene results in tolerance to subsequent exposure to donor antigen, and can thus induce tolerance to tissue from the donor. These methods, and other methods which can be combined with the methods disclosed herein, are discussed in Sachs, U.S. Ser. No. 08/126, 122, filed Sep. 23, 1993, and in Sachs, U.S. Ser. No. 08/220,371, filed Mar. 29, 1994.

Methods of inducing tolerance, e.g., by the implantation of hematopoietic stem cells, disclosed in Sachs, Cosimi, and Sykes, U.S. Ser. No. 07/838,595, filed Feb. 19, 1992, can also be combined with the methods disclosed herein.

Other methods of inducing tolerance can be combined with the methods disclosed herein to promote acceptance of donor tissue. For example, suppression of T cell help, which can be induced, e.g., by the administration of a short course of high dose immunosuppresant, e.g., cyclosporine, has been found to induce tolerance. In these methods, T cell help is suppressed for a comparatively short period just subsequent to implantation of a graft, and does not require or include chronic immunosuppression. These methods, as well as other methods which can be combined with the methods disclosed herein, are described in Sachs, U.S. Ser. No. 08/220,371, filed Mar. 29, 1994.

Other methods of promoting tolerance or promoting the acceptance of grafts, e.g., by altering levels of cytokine activity, are disclosed in Sachs, LeGuern, Sykes, and Blancho, U.S. Ser. No. 08/114,072, filed Aug. 30, 1993.

In another aspect, the invention features, a method of restoring or inducing immunocompetence in a recipient, e.g., a primate recipient, e.g., a human, at risk for an acquired immune disorder, (e.g., a human at risk for AIDS), which is thymus-function deficient and thus unable to produce a normal number of mature functional T cells or a sufficient number of mature functional T cells for a normal immune response. The invention includes the steps of introducing into the primate recipient, donor thymic tissue, preferably, xenogeneic thymic tissue, and donor hematopoietic stem cells, preferably xenogeneic hematopoietic stem cells, so that donor T cells can mature in the implanted donor thymic tissue. The thymic tissue is preferably fetal or neonatal thymic tissue.

In preferred embodiments the thymic graft is a xenograft and: the thymic xenograft is a discordant xenograft; the thymic xenograft is a concordant xenograft; the recipient is a human and the thymic tissue is vertebrate, e.g., swine, e.g., miniature swine, thymic tissue, or primate thymic tissue.

In preferred embodiments: the xenograft hematopoietic stem cells are from a discordant species; the hematopoietic stem cells are a concordant species; the recipient is a human and the hematopoietic stem cells are vertebrate, e.g., swine, e.g., miniature swine, hematopoietic stem cells, or primate hemopoietic stem cells.

In preferred embodiments the donor of the thymic graft and the donor of the stem cells are: the same organism; from the same species; syngeneic; matched at at least one MHC locus; matched at at least one class I MHC locus; matched at at least one class II MHC locus; sufficiently MHC matched that one will not reject a graft from the other; miniature swine from a herd which is completely or partially inbred.

Acceptance of donor tissue, especially xenogeneic tissue, will depend on the stage of the immune disorder. Generally, the more advanced the disorder the more compromised the recipient immune system and the easier it is to induce acceptance of donor tissue. In some cases, the tolerizing effect of the donor tissue itself will be sufficient to provide for acceptance. In other cases, additional measures will be needed. Thus, the method can include other steps which facilitate acceptance of donor tissue or otherwise optimize the method. In preferred embodiments: liver or spleen tissue, preferably fetal or neonatal liver or spleen tissue, is implanted with the thymic tissue; donor hemopoietic cells, e.g., cord blood cells or fetal or neonatal liver or spleen cells, are administered to the recipient, e.g., a suspension of fetal liver cells is administered intraperitoneally or intravenously; the recipient is thymectomized, preferably before or at the time the xenograft thymic tissue is introduced.

In preferred embodiments: the method includes, (preferably prior to or at the time of introducing the thymic tissue or stem cells into the recipient) depleting, inactivating or inhibiting recipient NK cells, e.g., by introducing into the recipient an antibody capable of binding to natural killer (NK) cells of the recipient, to prevent NK mediated rejection of the thymic tissue; the method includes, (preferably prior to or at the time of introducing the thymic tissue or stem cells into the recipient) depleting, inactivating or inhibiting recipient T cells, e.g., by introducing into the recipient an antibody capable of binding to T cells of the recipient mammal; (preferably prior to or at the time of introducing the thymic tissue or stem cells into the recipient) depleting, inactivating or inhibiting host $CD4^+$ cell function, e.g., by introducing into the recipient an antibody capable of binding to CD4, or $CD4^+$ cells of the recipient.

Other preferred embodiments include the step of (preferably prior to thymic tissue or hematopoietic stem cell transplantation) creating hematopoietic space, e.g., by one or more of: irradiating the recipient mammal with low dose, e.g., between about 100 and 400 rads, whole body irradiation, the administration of a myelosuppressive drug, the administration of a hematopoietic stem cell inactivating or depleting antibody, to deplete or partially deplete the bone marrow of the recipient.

Other preferred embodiments include (preferably prior to thymic tissue or hematopoietic stem cell transplantation) inactivating thymic T cells by one or more of: irradiating the recipient mammal with, e.g., about 700 rads of thymic irradiation, administering to the recipient one or more doses of an anti T cell antibody, e.g., an anti-CD4 and/or an anti-CD8 monoclonal antibody, or administering to the recipient a short course of an immunosuppressant, as is described in U.S. Ser. No. 08/220,371.

Other preferred embodiments include depleting or otherwise inactivating natural antibodies, e.g., by one or more of: the administration of a drug which depletes or inactivates natural antibodies, e.g., deoxyspergualin; the administration of an anti-IgM antibodies; or the absorption of natural antibodies from the recipient's blood, e.g., by contacting the hosts blood with donor antigen, e.g., by hemoperfusion of a donor organ, e.g., a kidney or a liver, from the donor species.

In preferred embodiments the host or recipient is a post-natal individual, e.g., an adult, or a child.

In preferred embodiments the method further includes the step of identifying a host or recipient which is at risk for an acquired immune disorder, (e.g., a human at risk for AIDS), and which is thymus-function deficient and thus unable to produce a normal number of mature functional T cells or a sufficient number of mature functional T cells for a normal immune response.

Other methods can be combined with the methods disclosed herein to promote the acceptance of donor tissue by the recipient. For example, tolerance to donor tissue can be induced by inserting a nucleic acid which expresses a donor antigen, e.g., a donor MHC gene, into a cell of the recipient, e.g., a hematopoietic item cell, and introducing the genetically engineered cell into the recipient. For example, human recipient stem cells can be engineered to express a swine MHC gene, e.g. a swine class I or class II MHC gene, or both a class I and a class II gene, and the cells implanted in a human recipient who will receive swine thymic tissue. When inserted into a recipient primate, e.g., a human, expression of the donor MHC gene results in tolerance to subsequent exposure to donor antigen, and can thus induce tolerance to tissue from the donor. These methods and other methods which can be combined with the methods disclosed herein are discussed in Sachs, U.S. Ser. No. 08/126, 122, filed Sep. 23, 1993, and in Sachs, U.S. Ser. No. 08/220,371, filed Mar. 29, 1994.

Methods of inducing tolerance, e.g., by the implantation of hematopoietic stem cells, disclosed in Sachs, Cosimi, and Sykes, U.S. Ser. No. 07/838,595, filed Feb. 19, 1992, can also be combined with the methods disclosed herein.

Other methods of inducing tolerance can be combined with the methods disclosed herein to promote acceptance of donor tissue. For example, suppression of T cell help, which can be induced, e.g., by the administration of a short course of high dose immunosuppresant, e.g., cyclosporine, has been found to induce tolerance. In these methods, T cell help is suppressed for a comparatively short period just subsequent to implantation of a graft, and does not require or include chronic immunosuppression. These methods, as well as other methods which can be combined with the methods disclosed herein, are described in Sachs, U.S. Ser. No. 08/220,371, filed Mar. 29, 1994.

Other methods of promoting tolerance or promoting the acceptance of donor tissue, e.g., by altering levels of cytokine activity, or inhibiting Graft-versus-recipient- disease, are disclosed in Sachs, LeGuern, Sykes, and Blancho, U.S. Ser. No. 08/114,072, filed Aug. 30, 1993.

It has also been discovered that hemopoietic cells can be use to induce tolerance to a graft.

Accordingly, in another aspect, the invention features, a method of inducing immunological tolerance in a recipient mammal, e.g., a primate, e.g., a human, of a first species to a graft obtained from a donor mammal of a second species, e.g., a discordant species e.g., a discordant primate species. The method includes: prior to or simultaneous with transplantation of the graft, introducing into the recipient mammal hematopoietic stem cells, e.g., bone marrow cells, or fetal liver or spleen cells, of the second species; (preferably, the hematopoietic stem cells home to a site in the recipient mammal); optionally, (preferably prior to introducing the hematopoietic stem cells into the recipient mammal), depleting, inactivating or inhibiting recipient NK cells, e.g., by introducing into the recipient mammal an antibody capable of binding to natural killer (NK) cells of the recipient mammal, to prevent NK mediated rejection of the hematopoietic cells; and (optionally) implanting the graft in the recipient. As will be explained in more detail below, the hematopoietic cells prepare the recipient for the graft that follows, by inducing tolerance at both the B-cell and T-cell levels. Preferably, hematopoietic cells are fetal liver or spleen, or bone marrow cells, including immature cells (i.e., undifferentiated hematopoietic stem cells; these desired cells can be separated out of the bone marrow prior to administration), or a complex bone marrow sample including such cells can be used.

One source of anti-NK antibody is anti-human thymocyte polyclonal anti-serum. A second, anti-mature T cell antibody can be administered as well, which lyses T cells as well as NK cells. Lysing T cells is advantageous for both bone marrow and xenograft survival. Anti-T cell antibodies are present, along with anti-NK antibodies, in anti-thymocyte anti-serum. Repeated doses of anti-NK or anti-T cell antibody may be preferable. Monoclonal preparations can be used in the methods of the invention.

Preferred embodiments include: the step of introducing into the recipient mammal, donor species-specific stromal tissue, preferably hematopoietic stromal tissue, e.g., fetal liver or thymus; and the step of prior to hematopoietic stem cell transplantation, introducing into the recipient mammal an antibody capable of binding to mature T cells of the recipient mammal.

Preferred embodiments include those in which: the stromal tissue is introduced simultaneously with, or prior to, the hematopoietic stem cells; the hematopoietic stem cells are introduced simultaneously with, or prior to, the antibody; the stromal tissue is introduced simultaneously with, or prior to, the hematopoietic stem cells, and the hematopoietic stem cells are introduced simultaneously with, or prior to, the antibody.

Preferred embodiments include those in which: the same mammal of the second species is the donor of both the graft and the hematopoietic cells; the donor mammal is a swine, e.g., a miniature swine; the introduction is by intravenous injection; and an anti-human thymocyte polyclonal antiserum, obtained, e.g., from a horse or pig is administered.

Other preferred embodiments include the step of (preferably prior to thymic tissue or hematopoietic stem cell transplantation) creating hematopoietic space, e.g., by one or more of: irradiating the recipient mammal with low dose, e.g., between about 100 and 400 rads, whole body irradiation, the administration of a myelosuppressive drag, the administration of a hematopoietic stem cell inactivating or depleting antibody, to deplete or partially deplete the bone marrow of the recipient.

Other preferred embodiments include (preferably prior to thymic tissue or hematopoietic stem cell transplantation) inactivating thymic T cells by one or more of: irradiating the recipient mammal with, e.g., about 700 rads of thymic irradiation, administering to the recipient one or more doses of an anti T cell antibody, e.g., an anti-CD4 and/or an anti-CD8 monoclonal antibody, or administering to the recipient a short course of an immunosuppressant, as is described in U.S. Ser. No. 08/220,371.

Other preferred embodiments include depleting or otherwise inactivating natural antibodies, e.g., by one or more of: the administration of a drug which depletes or inactivates natural antibodies, e.g., deoxyspergualin; the administration of an anti-IgM antibodies; or the absorption of natural antibodies from the recipient's blood, e.g., by contacting the hosts blood with donor antigen, e.g., by hemoperfusion of a donor organ, e.g., a kidney or a liver, from the donor species.

Preferred embodiments include: (preferably prior to hematopoietic stem cell transplantation) depleting, inactivating, or inhibiting recipient T cells, e.g., by introducing into the recipient an antibody capable of binding to mature T cells of the recipient.

Preferably the graft is obtained from a different organ than the hematopoietic stem cells.

Preferred embodiments include those in which: the primate is a eynomolgus monkey; the primate is a human; the stromal tissue is fetal or neonatal liver; the stromal tissue is fetal or neonatal thymus; the mammal is a swine; e.g., a miniature swine; the graft is a liver; the graft is a kidney.

Other methods can be combined with the methods disclosed herein to promote the acceptance of the graft by the recipient. For example, tolerance to the xenogeneic thymic tissue can also be induced by inserting a nucleic acid which expresses a donor antigen, e.g., a donor MHC gene, into a cell of the recipient, e.g., a hematopoietic stem cell, and introducing the genetically engineered cell into the recipient. For example, human recipient stem cells can be engineered to express a swine class I or class II MHC gene, or both a class I and II gene, and the cells implanted in a human recipient who will receive swine thymic tissue. When inserted into a recipient primate, e.g., a human, expression of the donor MHC gene results in tolerance to subsequent exposure to donor antigen, and can thus induce tolerance to thymic tissue from the donor. These methods, and other methods which can be combined with the methods disclosed herein, are discussed in Sachs, U.S. Ser. No. 08/126, 122, filed Sep. 23, 1993, and in Sachs, U.S. Ser. No. 08/220,371, filed Mar. 29, 1994.

Methods of inducing tolerance, e.g., by the implantation of hematopoietic stem cells, disclosed in Sachs, Cosimi, and Sykes, U.S. Ser. No. 07/838,595, filed February 19, 1992, can also be combined with the methods disclosed herein.

Other methods of inducing tolerance may also be used to promote acceptance of the xenogeneic thymic tissue. For example, suppression of T cell help, which can be induced, e.g., by the administration of a short course of high dose immunosuppresant, e.g., cyclosporine, has been found to induce tolerance. In these methods, T cell help is suppressed for a comparatively short period just subsequent to implantation of a graft, and does not require or include chronic immunosuppression. These methods, as well as other methods which can be combined with the methods disclosed herein, are described in Sachs, U.S. Ser. No. 08/220,371, filed Mar. 29, 1994, hereby incorporated by reference.

Other methods of promoting tolerance or promoting the acceptance of grafts, e.g., by altering levels of cytokine activity, are disclosed in Sachs, LeGuem, Sykes, and Blancho, U.S. Ser. No. 08/114,072, filed Aug. 30, 1993.

In another aspect, the invention features a method of inducing immunological tolerance in a recipient mammal, e.g., a primate, e.g., a human to a graft obtained from a donor mammal of the same species. The method includes the following: (preferably prior to or simultaneous with transplantation of the graft) introducing into the recipient mammal hematopoietic stem cells, e.g., bone marrow cells or fetal liver or spleen cells, obtained from a mammal (preferably, the hematopoietic stem cells home to a site in the recipient mammal); and, preferably, introducing the graft into the recipient.

Preferred embodiments include: the step of introducing into the recipient mammal, donor species-specific stromal tissue, preferably hematopoietic stromal tissue, e.g., fetal liver or thymus; and prior to hematopoietic stem cell transplantation, depleting, inactivating or inhibiting recipient T cells, e.g., by introducing into the recipient mammal an antibody capable of binding to mature T cells of the recipient mammal.

Other preferred embodiments include the step of (preferably prior to thymic tissue or hematopoietic stem cell transplantation) creating hematopoietic space, e.g., by one or more of: irradiating the recipient mammal with low dose, e.g., between about 100 and 400 rads, whole body irradiation, the administration of a myelosuppressive drug, the administration of a hematopoietic stem cell inactivating or depleting antibody, to deplete or partially deplete the bone marrow of the recipient.

Other preferred embodiments include (preferably prior to thymic tissue or hematopoietic stem cell transplantation) inactivating thymic T cells by one or more of: irradiating the recipient mammal with, e.g., about 700 rads of thymic irradiation, administering to the recipient one or more doses of an anti T cell antibody, e.g., an anti-CD4 and/or an anti-CD8 monoclonal antibody, or administering to the recipient a short course of an immunosuppressant, as is described in U.S. Ser. No. 08/220,371.

Other preferred embodiments include depleting or otherwise inactivating natural antibodies, e.g., by one or more of: the administration of a drug which depletes or inactivates natural antibodies, e.g., deoxyspergualin; the administration of an anti-IgM antibodies; or the absorption of natural antibodies from the recipient's blood, e.g., by contacting the hosts blood with donor antigen, e.g., by hemoperfusion of a donor organ, e.g., a kidney or a liver, from the donor species.

In other preferred embodiments; the method includes: (preferably prior to or at the time of introducing the thymic tissue into the recipient) depleting, inactivating or inhibiting recipient natural killer (NK) cells, e.g., by introducing into the recipient an antibody capable of binding to NK cells of the recipient, to prevent NK mediated rejection of the thymic tissue; (preferably prior to or at the time of introducing the thymic tissue into the recipient) depleting, inactivating or inhibiting host T cell function, e.g., by introducing into the recipient an antibody capable of binding to T cells of the recipient.

Other methods can be combined with the methods disclosed herein to promote tolerance to a graft. Methods of inducing tolerance, e.g., by the implantation of hematopoietic stem cells, disclosed in Sachs, Cosimi, and Sykes, U.S. Ser. No. 07/838,595, filed Feb. 19, 1992, can also be combined with the methods disclosed herein.

Other methods of inducing tolerance may also be used to promote acceptance of donor tissue. For example, suppression oft cell help, which can be induced, e.g., by the administration of a short course of high dose immunosuppresant, e.g., cyclosporine, has been found to induce tolerance. In these methods, T cell help is suppressed for a comparatively short period just subsequent to implantation of a graft, and does not require or include chronic immunosuppression. These methods, as well as other methods which can be combined with the methods disclosed herein, are described in Sachs, U.S. Ser. No. 08/220,371, filed Mar. 29, 1994.

Other methods of promoting tolerance or promoting the acceptance of grafts, e.g., by altering levels of cytokine activity, are disclosed in Sachs, LeGuern, Sykes, and Blancho, U.S. Ser. No. 08/114,072, filed Aug. 30, 1993.

At risk for AIDS, as used herein, refers to being HIV positive or having AIDS.

Restoring, inducing, or promoting immunocompetence, as used herein, means one or both of: (1) increasing the number of mature functional T cells in the recipient (over what would be seen in the absence of treatment with a method of the invention) by either or both, increasing the number of recipient-mature functional T cells or by providing mature functional donor-T cells, which have matured in the recipient; or (2) improving the immune- responsiveness of the recipient, e.g., as is measured by the ability to mount a skin response to a recall antigen, or improving the responsiveness of a of a T cell of the recipient, e.g., as measured by an in vitro test, e.g., by the improvement of a proliferative response to an antigen, e.g., the response to tetanus antigen or to an alloantigen.

A mature functional T cell, as used herein, is a T cell (of recipient or donor origin) which responds to microbial antigens and tolerant to recipient and donor tissue.

Restoring or inducing the thymus-dependent ability for T cell progenitors to mature into mature T cells, as used herein, means either or both, increasing the number of functional mature T cells of recipient origin in a recipient, or providing mature functional donor T cells to a recipient, by providing donor thymic tissue in which T cells can mature. The increase can be partial, e.g., an increase which does not bring the level of mature functional T cells up to a level which results in an essentially normal immune response or partial, e.g., an increase which falls short of bringing the recipient's level of mature functional T cells up to a level which results in an essentially normal immune response.

"Thymus-function deficient", as used herein, refers to a condition in which the ability of an individual's thymus to support the maturation of T cells is impaired as compared with a normal individual. Thymus deficient conditions include those in which the thymus or thymus function is essentially absent.

"Tolerance", as used herein, refers to the inhibition of a graft recipient's ability to mount an immune response, e.g., to a donor antigen, which would otherwise occur, e.g., in response to the introduction of a non self MHC antigen into the recipient. Tolerance can involve humoral, cellular, or both humoral and cellular responses. The concept of tolerance includes both complete and partial tolerance. In other words, as used herein, tolerance include any degree of inhibition of a graft recipient's ability to mount an immune response, e.g., to a donor antigen.

"A discordant species combination", as used herein, refers to two species in which hyperacute rejection occurs when vascular organs are grafted. Generally, discordant species are from different orders, while non-discordant species are from the same order. For example, rats and mice are non-discordant species, i.e. their MHC antigens are substantially similar, and they are members of the same order, rodentia.

"Hematopoietic stem cell", as used herein, refers to a cell that is capable of developing into mature myeloid and/or lymphoid cells. Preferably, a hematopoietic stem cell is capable of the long-term repopulation of the myeloid and/or lymphoid lineages.

"Miniature swine", as used herein, refers to completely or partially inbred miniature swine.

"Graft", as used herein, refers to a body part, organ, tissue, cells, or portions thereof.

"Stromal tissue", as used herein, refers to the supporting tissue or matrix of an organ, as distinguished from its functional elements or parenchyma.

An acquired immune deficiency is one which is due primarily to other than genetic defects.

Methods of the invention will allow the induction of immunocompetence in patients suffering from an immunodeficiency, e.g., a T cell deficiency, e.g., a thymic based immunodeficiency, e.g., a congenital immunodeficiency due to thymic aplasia or dysfunction, an acquired immune disorder, e.g., AIDS, immunoincompetence resulting form a neoplastic disease, or immunoincompetence resulting from a medical procedure, e.g., chemotherapy or radiation treatment.

Other features and advantages of the invention will be apparent from the following detailed description, and from the claims.

DETAILED DESCRIPTION

Drawings The drawings are first briefly described.

Figure 1A:
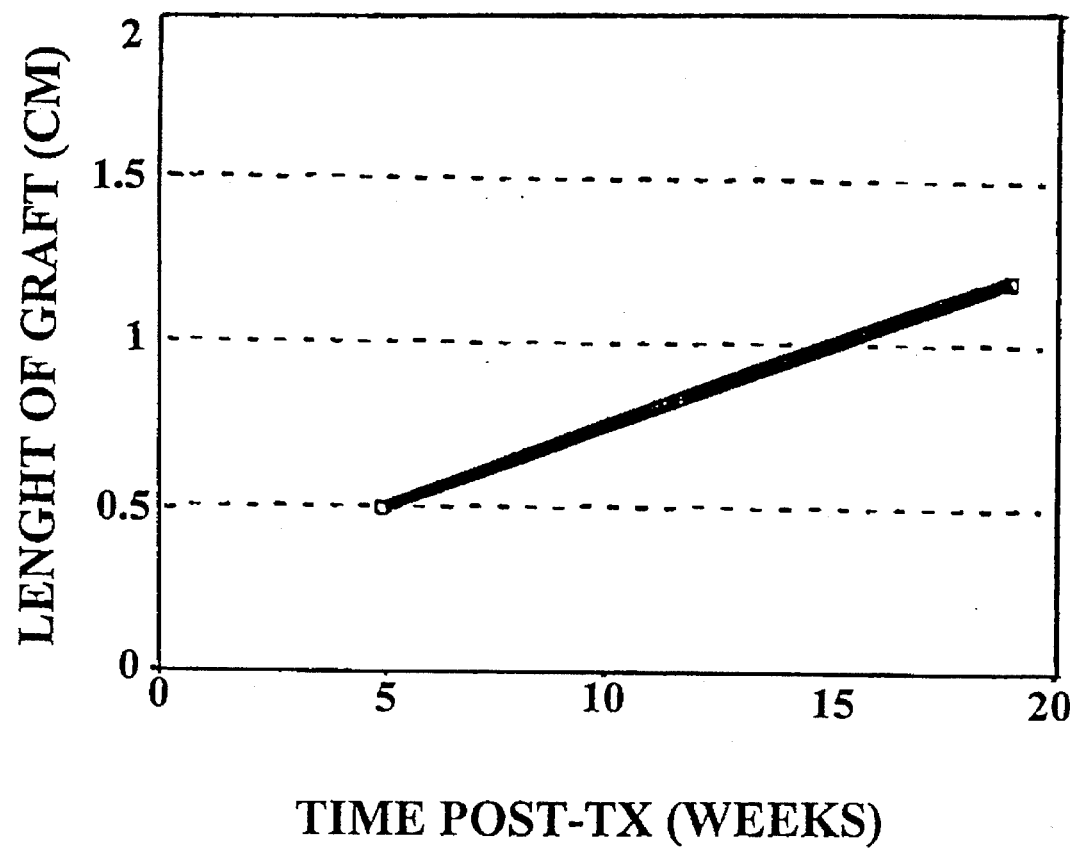

FIG. 1A is a graph showing growth of fetal pig THY/LIV graft vs. time after transplantation in the presence of mature mouse T cells in the periphery.

Figure 1B:
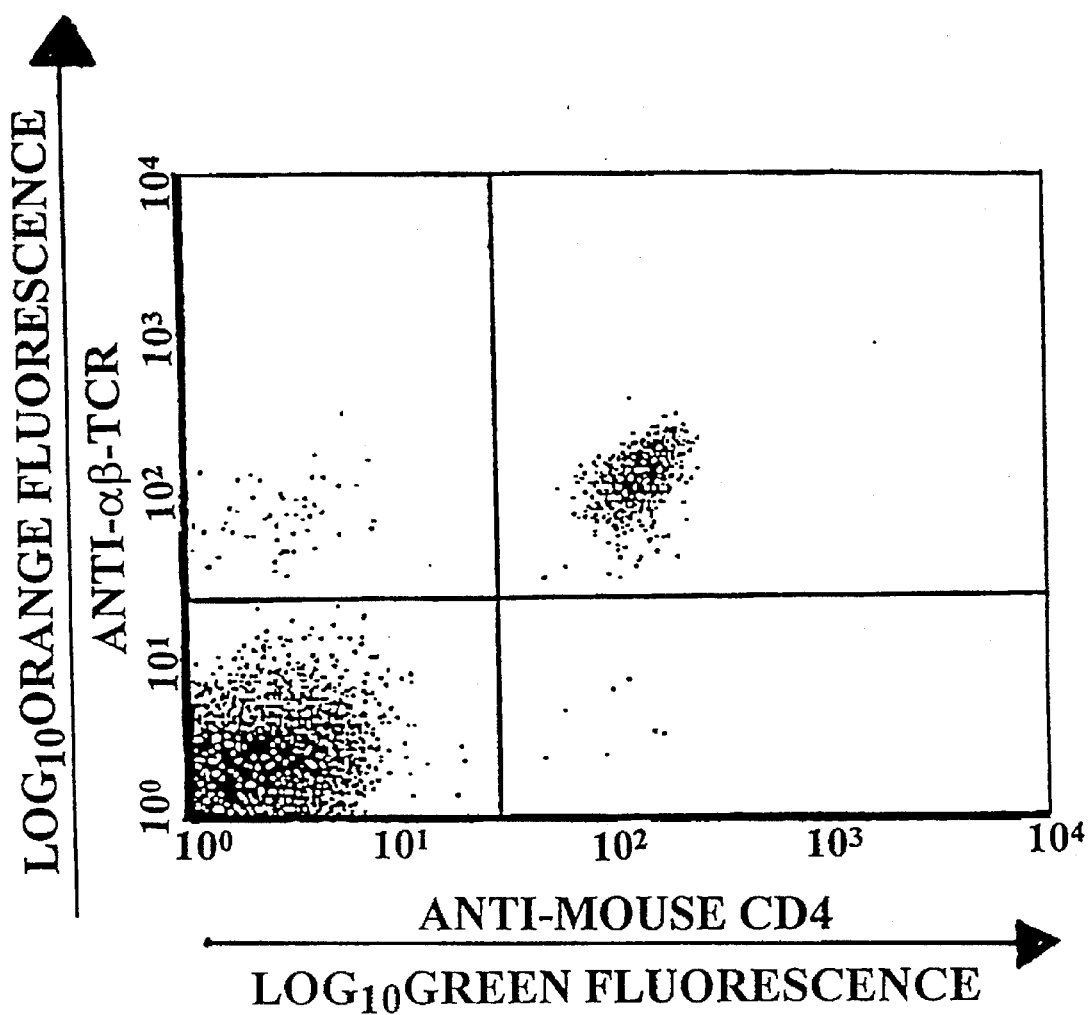

FIG. 1B is a dot plot analysis of live peripheral white blood cells of a representative animal 16 weeks/post-transplant. Upper left quadrant 0.5%; upper right quadrant 12.1%.

Figure 2:
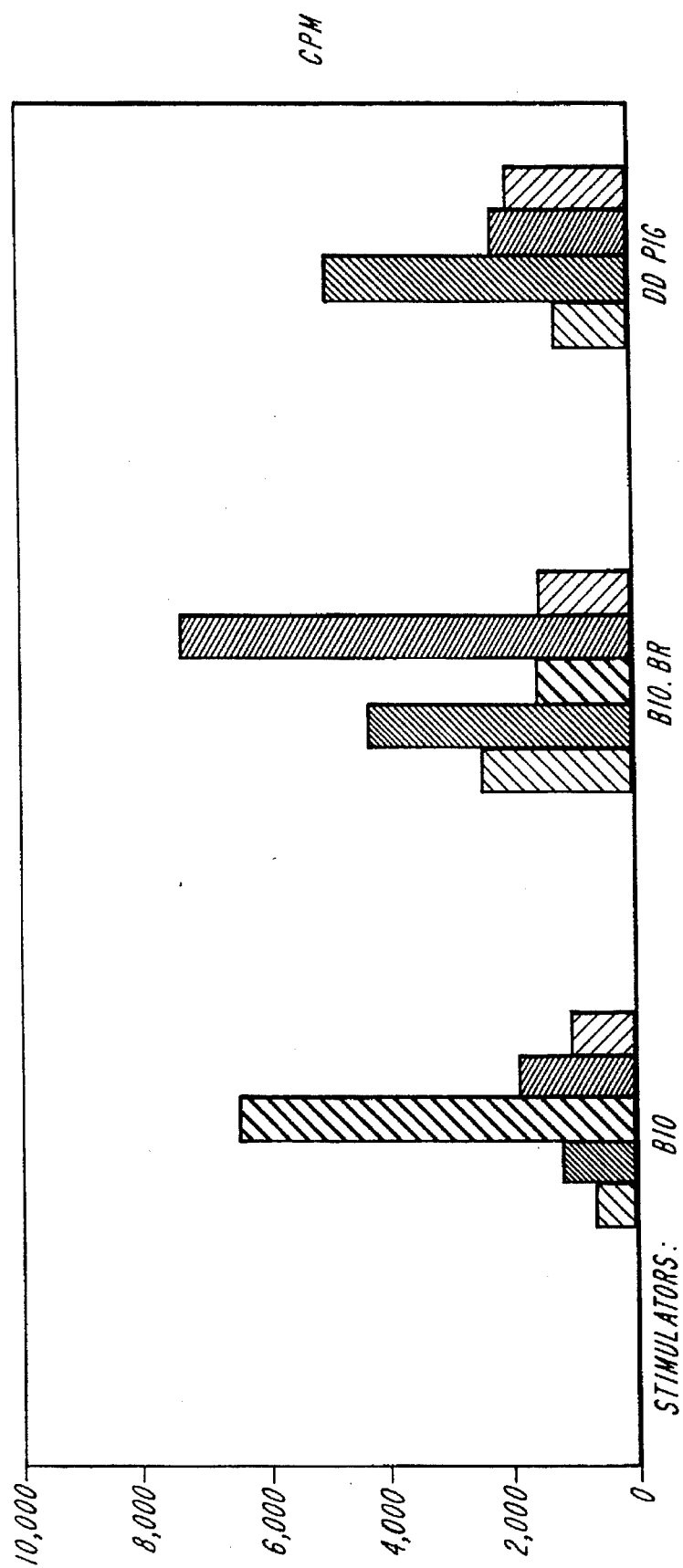

FIG. 2 is a graph of mouse anti-pig mixed lymphocyte reactions (MLR's) performed to determine whether or not mouse T cells which matured in pig thymus grafts were tolerant to pig antigens.

Maturation of host T cells in a xenogeneic thymus and induction of tolerance to a xenograft by xenogeneic thymic tissue The following procedure was designed to promote the acceptance of a xenograft thymus by a host and thusly to either or both: 1, lengthen the time an implanted organ (a xenograft) survives in a xenogeneic host prior to rejection; and 2, provide xenogeneic thymic tissue in which host T cells can mature.

In the case of an organ transplant, the organ can be any organ, e.g., a liver, e.g., a kidney, e.g., a heart. The two main strategies are elimination of natural antibodies and transplantation of thymic tissue to induce tolerance.

Preparation of the recipient for either organ transplantation or thymus replacement includes any or all of the following steps. Preferably they are carded out in the following sequence.

First, a preparation of horse anti-human thymocyte globulin (ATG) is intravenously injected into the recipient. The antibody preparation eliminates mature T cells and natural killer cells. If not eliminated, mature T cells might promote rejection of both the thymic transplant and, after sensitization, the xenograft organ. The ATG preparation also eliminates natural killer (NK) cells. NK cells probably have no effect on an implanted organ, but might act immediately to reject the newly introduced thymic tissue. Anti-human ATG obtained from any mammalian host can also be used, e.g., ATG produced in pigs, although thus far preparations of pig ATG have been of lower titer than horse-derived ATG. ATG is superior to anti-NK monoclonal antibodies, as the latter are generally not lytic to all host NK cells, while the polyclonal mixture in ATG is capable of lysing all host NK cells. Anti-NK monoclonal antibodies can, however, be used. In a relatively severely immuno-compromised individual this step may not be necessary. As host (or donor) T cells mature in the xenogeneic thymus they will be tolerant of the xenogeneic thymic tissue. Alternatively, as the host immune system is progressively restored, it may be desirable to treat the host to induce tolerance to the xenogeneic thymic tissue.

Optimally, the recipient can be thymectomized. In thymectomized recipients, recipient T cells do not have an opportunity to differentiate in the recipient thymus, but must differentiate in the donor thymus. In some cases it may be necessary to splenectomize the recipient in order to avoid anemia.

Second, the recipient can be administered low dose radiation. Although this step is thought to be beneficial in bone marrow transplantation (by creating hematopoietic space for newly injected bone marrow cells), it is of less importance in thymic grafts which are not accompanied by bone marrow transplantation. However, a sublethal dose e.g., a dose about equal to 100, or more than 100 and less than about 400, rads, whole body radiation, plus 700 rads of local thymic radiation, can be used.

Third, natural antibodies can be absorbed from the recipient's blood. (This is of more importance in organ grafts but can be used in thymus replacement procedures as well.) Antibody removal can be accomplished by exposing the recipient's blood to donor or donor species antigens, e.g., by hemoperfusion of a liver of the donor species to absorb recipient- natural antibodies. Pre-formed natural antibodies (nAb) are the primary agents of graft rejection. Natural antibodies bind to xenogeneic endothelial cells and are primarily of the IgM class. These antibodies are independent of any known previous exposure to antigens of the xenogeneic donor. B cells that produce these natural antibodies tend to be T cell- independent, and are normally tolerized to self antigen by exposure to these antigens during development. The mechanism by which newly developing B cells are tolerized is unknown. The liver is a more effective absorber of natural antibodies than the kidney. Again, this step may not be required, at least initially, in a relatively severely immuno-compromised patient.

Donor thymic tissue, preferably fetal or neonatal thymic tissue is implanted in the recipient. Fetal or neonatal liver or spleen tissue can be included.

While any of these procedures may aid the survival of implanted thymic tissue or another xenogeneic organ, best results are achieved when all steps are used in combination.

Methods of the invention can be used to confer tolerance to allogeneic grafts, e.g., wherein both the graft donor and the recipient are humans, and to xenogeneic grafts, e.g., wherein the graft donor is a nonhuman animal, e.g., a swine, e.g., a miniature swine, and the graft recipient is a primate, e.g., a human.

The donor of the implant and the individual that supplies the tolerance-inducing thymic graft should be the same individual or should be as closely related as possible. For example, it is preferable to derive implant tissue from a colony of donors that is highly or completely inbred. The donor of the organ used for perfusion need not be closely related to the donor of the implant or thymic tissue.

Xenograft Thymic Tissue Transplantation: Detailed Protocol

Immunocompetent C57BL/10 (B10) mice were used to test the ability of pig thymus to induce specific tolerance to discordant pig antigens. B10 mice were treated with a non-myeloablative conditioning regime which has previously shown to permit induction of tolerance to rat xenoantigens in mice, see e.g., Sharabi et at., 1990, J. Exp. Med. 172:195–202. Euthymic or thymectomized (ATX) mice received depleting doses of anti-T cell and anti-NK cell mAbs, 7 Gy mediastinal irradiation and 3 Gy whole body irradiation (WBI), and then received fetal swine thymus/liver (THY/LIV) transplants under the kidney capsule followed by administration of $10^8$ fetal liver cells (FLC) i.p. Mice either received no further anti-T cell and anti-NK cell mAb treatments after 0 to 6 weeks post-tx, or were maintained on chronic mAb treatment for the duration of the experiment.

Swine THY/LIV grafts grew initially in treated euthymic mice, but stopped growing after T cell and natural killer (NK) cell-depleting monoclonal antibodies (mAbs) were discontinued, and these mice developed anti-pig IgG response. When euthymic mice were maintained on chronic mAb treatment, the grafts enlarged markedly and no anti-pig IgG response was observed. Pig thymospoiesis was supported for at least 32 weeks during chronic mAb administration, although no pig T cells were detected in the periphery by flow cytometry (FMC). Percentages of intragraft $CD4^+/CD8^-$, $CD4^-/CD8^+$, $CD4^+/CD8^+$, and $CD^-/CD8^-$ pig thymocyte subsets were similar to those in normal pig thymus.

In contrast, swine THY/LIV grafts grew markedly in adult thymectomized mice (ATX-THY/LIV) which received only a short (less than 6 weeks) course of mAb treatment post-transplant Loost-tx). FCM analysis of peripheral WBC in these mice 6 weeks after discontinuing mAb treatment revealed the presence of mature ($\alpha\beta$-TRC$^{hi}$) mouse T cells. Unlike T cells in euthymic grafted mice, these cells were tolerant to pig antigens, as evidenced by the growth of swine THY/LIV grafts, (FIG. 1), and the absence of anti-pig IgG antibody responses. The majority (more than 90%) of the $\alpha\beta$-TCR$^{hi}$ T cells were CD4$^+$/CD8$^-$. FMC analyses 13 to 26 weeks post-tx demonstrated normal mouse thymocyte subsets in swine thymi. For example, 7.9% CD4$^+$/CD8$^-$, 2.9% CD4$^-$/CD8$^+$, 85.5% CD4$^+$/CD8$^+$, 3.7% CD4$^-$/CD8$^-$ and 11.6% $\alpha\beta$-TCR$^{hi}$ thymocytes in a normal B10 thymus. Fetal swine liver grafted without a thymus fragment did not grow in control mAb-treated ATX-B10 mice and $\alpha\beta$-TCT$^{hi}$ T cells did not appear in the periphery. Thus, the pig thymus was required for the development of mature mouse T cells.

Mouse anti-pig mixed lymphocyte reactions (MLR's) were performed to determine whether or not mouse T cells which matured in pig thymus grafts were tolerant to pig antigens. ATX-THY/LIV B10 mice (H-2$^b$) mounted no anti-B10 or anti-pig responses, but demonstrated normal allo-responses against a fully MHC-mismatched allogeneic stimulator, B10.BR (H-2$^k$) (FIG. 2).

In order to determine if host bone marrow-derived cells were participating in negative selection of the developing mouse thymocytes, fetal pig THY/LIV grafts were transplanted into both I-E$^+$ (BALB/c nude) and I-E$^-$ (ATX B10) recipients. I-E$^+$ mice delete V$_\beta$11 T cells because of presentation in the thymus of an endogenous superantigen in association with I-e, whereas I-E$^-$ mice do not delete this T cell family. The percentages of V$_\beta$11 T cells were therefore compared between I-E$^+$ and I-E$^-$ recipients of fetal pig thymus grafts in which murine T cells developed in pig thymi. ATX B10 recipients were treated as described above. BALB/c nude mice were depleted of NK cells and irradiated with 3 Gy WBI prior to transplant. These mice also developed large numbers of mature CD4$^+$ T cells that migrated to the periphery. Complete deletion of V$_\beta$11 T cells was observed in the periphery of BALB/c nude recipients of fetal swine thymus grafts (Table I), indicating that mouse I-E also participated in negative selection of mouse T cells developing in pig thymi. Negative selection is most likely carried out by murine Ia$^+$ dendritic cells which were detected predominantly in the cotrico-medullary junction of swine thymus grafts by immunoperoxidase staining. In the ATX B10 recipients of swine THY/LIV grafts, reduction in the percentage of V$_\beta$11 T cells was observed compared to normal B10 mice (mean 2.8% of T cells±0.8 S.D., normal B10 5.2%, p<0.005) suggesting that the pig SLA DR class II, which shares significant hornology with mouse I-E class II, may participate in negative selection of mouse T cells developing in the pig thymus graft (Table I).

TABLE I

| N | Strain | Thy/Liv Graft | % V$_\beta$8.1/8.2 | % V$_\beta$11 |
| --- | --- | --- | --- | --- |
| 4 | Normal C57BL/10 | – | 16.3 ± 2.2 | 5.2 ± 0.5 |
| 4 | Normal BALB/c | – | 20.8 ± 0.3 | 0.2 ± 0.1 |
| 4 | C57BL/10 | + | 16.7 ± 3.0 | 2.8 ± 0.8 |
| 5 | BALB/c nude | + | 20.0 ± 3.7 | 0.4 ± 0.3 |

Table I. Clona deletion in mice transplanted with swine THY/LIV grafts. B10 recipients were treated as described below. Normal percentages of T cells staining with V$_\beta$8.1/8.2 demonstrates normal positive selection in grafted mice of a V$_\beta$T cell family which is not deleted in I-E$^+$ or I-E$^-$ mice. BALB/c nude mice were depleted of NK cells using rabbit anti-Asiao-Gm1 serum, and were given 3 Gy WBI, and fetal swine THY/LIV grafts implants under the kidney capsule, followed by injection of $10^8$ FLC i.p. on Day 0. ACK-lysed splenocytes or peripheral white blood cells (red blood cells were removed by hypotonic shock) were collected 13 to 19 weeks post-Ix and analyzed by FCM for V$_\beta$11 T cell deletion. Murine F$_c$R's were blocked using rat anti-mouse F$_c$R mAb, 2.4G2, and then cells were stained with either fluoresceinated hamster anti-mouse V$_\beta$8.1/8.2 TCR (Pharmingen) or rat anti-mouse V$_\beta$11 TCR (Pharmingen) (green fluorescence) followed by phycoerythrin-conjugated rat anti-mouse CD4 and CD8 mAbs (Pharmingen) (orange fluorescence) and analyzed by two color FCM as described below. Fluoresceinated murine mAb HOPCI, with no known reactivity to mouse cells, or rat anti-mouse IgGl (Zymed Laboratories, Inc.) was used as the negative control mAb in the green fluorescence. Phycoerythrin-conjugated mAb Leu-4 (Becton-Dickinson), was used as the negative control mAb in the orange fluorescence. Approximately 5,000 gated CD4$^+$ and CD8$^+$ cells were usually collected for analysis of V$_\beta$ families. Nonviable cells were excluded using the vital nucleic acid stain, propidium iodide. Percentages of positive cells were determined as described below. Results are presented as the mean±SD of results obtained for individual mice. p value <0.005 for % $V_\beta 11$ in normal B10 mice compared to THY/LIV-grafted B10 mice. p value is >0.20 for % $V_\beta 11$ in normal BALB/c mice compared to THY/LIV-grafted BALB/c nude mice.

These studies demonstrate that discordant xenogeneic thymic stroma is capable of supporting mouse thymopoiesis and that $CD4^+/CD8^-/\alpha\beta-TCR^{hi}$ T cells which are released into the periphery are phenotypically normal, functional and tolerant to donor xeno-antigens, and to host antigens. The lack of $CD4^-/CD8^+/\alpha\beta-TCR^{hi}$ repopulation in the periphery may be due to failure of mouse CD8 to interact with pig MHC class I molecules, as has been demonstrated for mouse anti-human responses, thereby preventing positive selection of $CD8^+$ thymocytes by swine thymic epithelium. Since human $CD8^+$ T cells are able to interact with pig MHC class I directly, human $CD8^+$ T cells should mature effectively in swine fetal thymus grafts.

Presumably, tolerance to pig antigens is not induced in euthymic mice which receive swine THY/LIV grafts because mouse T cell progenitors mature in the host thymus, which lacks the pig cells necessary to tolerize developing mouse thymocytes. The non-myeloablative conditioning regime used in this study permits engraftment of rat marrow and induction of donor-specific tolerance in murine recipients. Tolerance is thought to be induced in this model by rat dendritic cells detected at the cortico-medullary junction of the thymus of chimeric animals. In the present study, failure of pig hematopoietic stem cells, present in the FLC suspension administered on Day 0, to migrate to the mouse thymus may be due to failure of homing and differentiation, possibly reflecting species specificity of cytokines and adhesion molecules. In ATX recipients, on the other hand, mouse T cell progenitors home to the pig thymus graft and are tolerized pig antigens. No mouse TE is present in ATX hosts, but mouse denaritic cells are detectable in THY/LIV grafts and probably mediate the observed clonal deletion of cells reactive to host antigen. Although the decreased percentage of $V_\beta 11$ T cells in ATX B10 recipients of swine THY/LIV grafts suggests clonal deletion by swine cells, it is possible that there is a defect in the positive selection of this $V_\beta$ family on swine thymic stroma. However, the normal percentages of $V_\beta 8.1/8.2$ T cells in both ATX B10 and BALB/c nude recipients of swine THY/LIV grafts compared to those in normal B10 and BALB/c mice suggests that no defect in positive selection is present. The observed tolerance could be explained if the swine thymic stroma either clonally deletes or anergizes developing mouse thymocytes reactive to donor xeno-antigens.

Survival of swine THY/LIV grafts in euthymic and thymectomized B10 mice depleted of T cells and NK cells, was determined as follows. 6-12 week old euthymic or ATX C57BL/10 (B10) mice received i.p. injections of mAbs GK 1.5 (anti-mouse CD4), 2.43 (anti-mouse CD5), 30-H12 (anti-mouse Thy1.2) and PK136 (anti-mouse NK1.1) in depleting doses, as described in Sharabi et at., on days −6 and −1 prior to transplantation. On either day −1 or day 0, 7 Gy localized thymic irradiation and 3 Gy whole body irradiation were administered to recipients, and second trimester (gestational day 36–72) fetal thymic and liver fragments, approximately 1 mm³ in size, were transplanted under the kidney capsule via a midline laparotomy incision. (Thymic irradiation was not found to be necessary for mouse T cells to mature in pig thymus grafts in subsequent experiments, and was therefore eliminated from the conditioning regimen.) After the abdomen was closed in two layers, $10^8$ fetal liver cells (FLC) in suspension were injected i.p. Recipients were treated on a weekly basis post-tx with depleting doses of the same four mAbs for a period of 0–6 weeks. No difference in murine $CD4^+$ T cell reconstitution Or tolerance to pig antigens was observed in mice which were treated with no mAb post-Ix compared to those which received 6 weeks mAb treatment post-tx. Some groups of control mice were maintained on chronic mAb treatment until the time of sacrifice.

As described above, an increase in fetal pig THY/LIV graft size was observed upon exploratory laparotomy performed at 5 and 19 weeks post-Ix, despite the presence of mature $CD4^+/\alpha\beta TCR^{hi}$ T cells in the peripheral blood (shown 16 weeks after mAbs were discontinued). Growth of fetal pig THY/LIV graft in the presence of mature mouse T cells in the periphery was studied as follows. Peripheral WBC contained 12.1% $CD4^+/\alpha\beta-TRC^{hi}$ T cells and 0.5% $CD8^+/\alpha\beta-TRC^+$ T cells. Control ATX mice which received fetal swine liver grafts without a thymus fragment did not maintain their grafts, and developed less than 5% $\alpha\beta-TRC^+$ T cells in the periphery. ATX mice were conditioned as described above. Exploratory laparotomies were performed at 5–6 and 15–19 weeks post-transplant to measure graft size. Mice were tail bled at regular intervals post-Ix to obtain peripheral WBC which were prepared by hypotonic shock to remove red blood cells. Cells were stained with a fluoresceinated rat anti-mouse CD4 mAb (Pharmigen) (green fluorescence) versus biotinylated hamster anti-mouse $\alpha\beta TRC$ mAb (Pharmigen) plus phycoerythrin streptavidin (orange fluorescence) and analyzed by two-color flow cytometry (FCM) using either a FACScan or FACSort flow cytometer (Becton-Dickinson). Murine mAb HOPC1, with no known reactivity to pig or mouse cells, was used as the negative control mAb in both the green and orange fluorescence. Percentages of positive cells were determined by subtracting the percentage of cells staining with the control mAb HOPC1 from the percentage of cells staining with the anti-mouse mAbs. A dot plot analysis of live peripheral white blood cells of a representative animal 16 weeks post-Ix (16 weeks after mAbs were discontinued) is shown in FIG. 2. Overall, 57% (²⁷/₄₇) of ATX mice treated with this protocol maintained swine grafts and reconstituted their $CD4^+$ T cell compartment. In recent experiments this result was achieved in 90% (⁹/₁₀) of mice treated with this regimen.

As described above, ATX-THY/LIV B10 ($H-2^b$) mice demonstrated specific unresponsiveness to pig antigens while maintaining normal allo-responsiveness to a fully MHC-mismatched B10.BR ($H-2^k$) stimulator. Specific unresponsiveness of B10 mice transplanted with fetal pig THY/LIV grafts to pig antigens in mixed lymphocyte reaction (MLR) was determined as follows. Control ATX-B10 mice which received a swine liver graft without a thymus fragment (ATX-LIV) mounted no responses to any stimulator, demonstrating the importance of the pig thymus graft in the development of functional mouse T cells. Positive control anti-pig MLR was from a mouse immunized with a swine skin graft, since mice do not mount primary anti-pig responses. Sterile splenocyte suspensions from normal B10 (right diagonal bar), normal B10 grafted with GG ($SLA-I^c$/$SLA-II^d$) pig skin 12 weeks earlier (GG'-B10 solid bar), normal B10BR (crosshatched bar), and thymectomized B10 mice conditioned with the non-myeloablative regimen described above and transplanted with either a fetal pig ($SLA-I^d$/$SLA-II^d$) THY/LIV graft (ATX-THY/LIV stippled bar), or a fetal pig liver graft only (ATX-LIV left diagonal bar) were ACK-lysed, washed and reconstituted in RPMI medium supplemented with 15% CPSR-2 (controlled processed serum replacement, Sigma), 4% nutrient mixture (L-glutamine, nonessential amino acids, sodium pyrovale and penlcillin/streptomycin), 1% HEPES buffer and $10^{-5}$ M 2-me. Swine PBL were prepared by centrifugation over a Ficoll-Hypaque layer. $4 \times 10^5$ responders were incubated with either $4 \times 10^5$ murine stimulators (3 Gy) or $1 \times 10^5$ swine stimulators (3 Gy) in a total volume of 0.2 ml of media at 37° C. for 4 days in 5% $CO_2$. Cultures were pulsed with 1 μCi $^3$H on the third day, harvested on the fourth day with a Tomtee automated harvester and counted on a Pharmacia LKB liquid scintillation counter. MLR's for all mice tested (N=3) were set up in duplicate and pulsed on Days 3 and 4 and harvested on Days 4 and 5 with similar results.

Thus, if murine T cells are permitted to develop in a mouse thymus, they are not tolerized to pig antigens, and they reject pig thymus/liver grafts. (Thus, if the recipient has significant thymic function thymectomy is indicated.) If mouse T cells are continually depleted by mAb, swine thymopoiesis occurs in the swine thymus/liver graft. If a mouse is thymectomized but not chronically treated with anti-T cell mAb's, mouse thymopoiesis occurs in the pig thymus, and these cells are tolerized to pig antigens.

Host T cells which mature in a xenogeneic thymus are functional

B10.BR (full MHC mismatch to B10) and C3H.SW (minor antigen mismatch only) skin grafts (1 mouse) were rejected by mouse T cells which had matured in a pig thymic graft, thus demonstrating their immunocompetence and ability to recognize minor antigens in a host MHC-restricted fashion. The grafts were full thickness tail skin grafts on the upper thorax with a skin bridge separating them. These results show that swine fetal thymic tissue can be used clinically to induce a state of specific xenograft tolerance while ensuring immunocompetence in thymectomized recipients.

Alternative Preparative Regimens

As is stated above, the depletion of NK cells, whole body irradiation, and thymic irradiation, can in some cases be dispensed with. As is shown by the experiments summarized below, inactivation or depletion of $CD4^+$ cells, e.g., by the administration of an anti-CD4 antibody, is sufficient to allow growth of xenogeneic thymic tissue and maturation of host T cells in the xenogeneic thymic tissue. (The antibodies needed may differ depending on the species combination. E.g., in the case of a human recipient and a pig donor, because human CD8 will likely interact with pig class I molecules, it may also be necessary to administer anti-CD8 antibodies.)

As is shown by the data in Table II below, graft growth and host T cell development (as measured by the presence of peripheral T cells 9 and 10 weeks post THY/LIV transplant) was seen in ATX mice treated with anti-CD4 antibodies and whole body irradiation. B10 mice received 3 Gy whole body irradiation and fetal pig THY/LIV graft and $10^8$ fetal liver cells in experiments essentially similar to those described in the previous section except that anti-CD4, anti-THY1.2, and anti NK cell antibodies were not administered.

TABLE II

THY/LIV graft growth and T cell maturation does not require extensive antibody treatment.

| Animal # | TREATMENT | GRAFT L/R | % CD4$^+$/% CD8$^+$ T CELLS/(WBC) |
|---|---|---|---|
| 639/44 | NO ATX/αCD4/8/ THY1.2/NK1.1 | | 17.7/4.6 |
| 643/02 | NO ATX/αCD4/8/ THY1.2/NK1.1 | | 9.4/2.6 |
| 601/02 | ATZ + /α CD4/8/THY1,2/NK1.1 | +/++ | 11.1/0.8 |
| 603/04 | ATZ + /α CD4/8/THY1,2/NK1.1 | +/+ | 1.7/1.2 |
| 605/06 | ATZ + /α CD4/8/THY1,2/NK1.1 | −/− | 0.6/0.3 |
| 607/08 | ATZ + /α CD4/8/THY1,2/NK1.1 | ++/++ | 0.9/0.6 |
| 609/10 | ATZ + /α CD4/8/THY1,2/NK1.1 | ++/+ | 1.8/0.5 |
| 611/12 | ATZ + /α CD4/8/THY1,2/NK1.1 | ++/++ | 3.4/1.6 |
| 615/16 | ATX + αCD4/8 | +/++ | 8.9/0.7 |
| 617/18 | ' | +/− | 2.1/0.3 |
| 619/20 | ' | ++/++ | 20.2/1.5 |
| 621/22 | ' | +/− | 1.1/0.1 |
| 623/24 | ' | ++/++ | 6.8/0.3 |
| 625/26 | ATX + αCD4 | ++/− | 7.2/4.0 |
| 627/28 | ' | −/+ | 1.0/5.1 |
| 629/30 | ' | ++/++ | 10.1/3.7 |
| 631/32 | ' | ++/+ | 3.7/3.5 |
| 633/34 | ' | −/− | 0.4/3.7 |
| 635/36 | ' | ++/++ | 28.0/4.2 |

ATX = thymectomy;
++ = large, bulky graft with vascularization;
+ = moderate sized graft;
− = poor graft (thin, poor tissue);
αCD4/8/THY1.2/NK1.1 indicates the administration of the descibed antibody.

As is shown by the data in Table III below, graft growth was seen in ATX mice treated with monoclonal antibodies but given no irradiation. In these experiments, B10 mice were given anti-CD4, CDS, THY1.2, and NK1.1 monoclonal antibodies.

TABLE III

THY/LIV graft growth does not require host irradiation.

| Animal # | TREATMENT | GRAFT L/R |
|---|---|---|
| 560/61 | ATX + mAb's + 3 Gy WBI | ++/++ |
| 562/63 | ' | +/++ |
| 564/65 | ' | −/− |
| 566/67 | ' | −/+ |
| 574/75 | ' | −/− |
| 576/77 | ' | −/− |
| 578/79 | ' | −/− |
| 582/83 | ' | +/− |
| 552/53 | ATX + mAb's (no WBI) | +/− |
| 554/55 | ' | ++/− |
| 556/57 | ' | ++/+ |
| 568/69 | ' | ++/++ |
| 570/71 | ' | ++/++ |

As is shown by the data in Table IV below, host T cell development (as measured by the presence of peripheral T cells 7 weeks post THY/LIV transplant) was seen in ATX mice given no irradiation and treated only with anti-CD4 antibodies.

TABLE IV

Rapid T Cell recovery in THY/LIV graft recipients
with thymectomy and anti CD4 antibodies alone.

| Number of animals in group # | TREATMENT | Mean % (SD) peripheral blood T cells at 7 weeks post transplant | |
|---|---|---|---|
| | | CD4+ | CD8+ |
| 3 | NO ATX αCD4/8/THY1.2/NK1.1 +3 Gy WBI | 12.9(1.7) | 2.7(0.1) |
| 8 | ATX αCD4/8/THY1.2/NK1.1 +3 Gy WBI | 3.4(2.4) | 0.7(0.5) |
| 7 | ATX αCD4/ | 19.5(3.4) | 7.1(1.8) |

Xenogeneic Thymic Tissue and Stem Cell Transplantation

The following procedure introduces donor thymic tissue and donor stem cells into the recipient and thus can be used to restore or induce immune function or to lengthen the time an implanted organ (a xenograft) survives in a xenogeneic host prior to rejection.

In the case of an organ graft, the organ can be any organ, e.g., a liver, e.g., a kidney, e.g., a heart. The two main strategies are elimination of natural antibodies by organ perfusion, and transplantation of tolerance-inducing bone marrow.

Preparation of the recipient includes any or all of the following steps. Preferably they are carried out in the following sequence.

Elimination of NK and T cells. First, a preparation of horse anti-human thymo cyte globulin (ATG) is intravenously injected into the recipient. The antibody preparation eliminates mature T cells and natural killer cells. If not eliminated, mature T cells would promote rejection of both the bone marrow transplant and, after sensitization, the xenograft itself. Of equal importance, the ATG preparation also eliminates natural killer (NK) cells. NK cells probably have no effect on the implanted organ, but would act immediately to reject the newly introduced bone marrow. Anti-human ATG obtained from any mammalian host can also be used, e.g., ATG produced in pigs, although thus far preparations of pig ATG have been of lower liter than horse-derived ATG. ATG is superior to anti-NK monoclonal antibodies, as the latter are generally not lytic to all host NK cells, while the polyclonal mixture in ATG is capable of lysing all host NK cells. Anti-NK monoclonal antibodies can, however, be used.

Thymic tissue transplant. In cases where the procedure is to restore or induce immuno competence donor thymic tissue (preferably fetal or neonatal thymic tissue) is implanted in the recipient so that donor T cells (and recipient T cells if the are present and functional) can mature. Fetal or neonatal liver or spleen tissue can be implanted with the thymic tissue.

The presence of donor antigen in the thymus during the time when host T cells are regenerating post-transplant is critical for tolerizing host T cells. If donor hematopoietic stem cells are not able to become established in the host thymus and induce tolerance before host T cells regenerate repeated doses of anti-recipient T cell antibodies may be necessary throughout the non-myeloablative regimen. Continuous depletion of host T cells may be required for several weeks. Alternatively, e.g., if this approach is not successful, and tolerance (as measured by donor skin graft acceptance, specific cellular hyporesponsiveness in vitro, and humoral tolerance) is not induced in these animals, the approach can be modified to include host thymectomy. In thymectomized recipients, host T cells do not have an opportunity to differentiate in a host thymus, but must differentiate in the donor thymus. Immunocompetence can be measured by the ability to reject a non-donor type allogeneic donor skin graft, and to survive in a pathogen-containing environment.

It may also be necessary or desirable to splenectomize the recipient in order to avoid anemia.

Creation of hematopoietic space. The recipient is administered low dose radiation in order to make room for newly injected bone marrow cells. A sublethal dose e.g., a dose about equal to 100, or more than 100 and less than about 400, rads, whole body radiation, plus 700 rads of local thymic radiation, has been found effective for this purpose.

Natural antibody elimination. Natural antibodies are absorbed from the recipient's blood by hemoperfusion of a liver of the donor species. Pre-formed natural antibodies (nAb) are the primary agents of graft rejection. Natural antibodies bind to xenogeneic endothelial cells and are primarily of the IgM class. These antibodies are independent of any known previous exposure to antigens of the xenogeneic donor. B cells that produce these natural antibodies tend to be T cell-independent, and are normally tolerized to self antigen by exposure to these antigens during development. The mechanism by which newly developing B cells are tolerized is unknown. The liver is a more effective absorber of natural antibodies than the kidney.

Implantation of donor stromal tissue. The next step in the non-myeloablative procedure is to implant donor stromal tissue, preferably obtained from fetal liver, thymus, and/or fetal spleen, into the recipient, preferably in the kidney capsule. Stem cell engraftment and hematopoiesis across disparate species barriers is enhanced by providing a hematopoietic stromal environment from the donor species. The stromal matrix supplies species-specific factors that are required for interactions between hematopoietic cells and their stromal environment, such as hematopoietic growth factors, adhesion molecules, and their ligands.

Each organ includes an organ specific stromal matrix that can support differentiation of the respective undifferentiated stem cells implanted into the host. Although adult thymus may be used, fetal tissue obtained sufficiently early in gestation is preferred because it is flee from mature T lymphocytes which can cause GVHD. Fetal tissues also tend to survive better than adult tissues when transplanted. As an added precaution against GVHD, thymic stromal tissue can be irradiated prior to transplantation, e.g., irradiated at 1000 rads. As an alternative or an adjunct to implantation, fetal liver cells can be administered in fluid suspension.

Finally, bone marrow cells (BMC), or another source of hematopoietic stem cells, e.g., a fetal liver suspension, or cord blood stem cells, of the donor are injected into the recipient. Donor stem cells home to appropriate sites of the recipient and grow contiguously with remaining host cells and proliferate, forming a chimeric lymphohematopoietic population. By this process, newly forming B cells (and the antibodies they produce) are exposed to donor antigens, so that the transplant will be recognized as self. Tolerance to the donor is also observed at the T cell level in animals in which hematopoietic stem cell, e.g., BMC, engraftment has been achieved. When an organ graft is placed in such a recipient several months after bone marrow chimerism has been induced, natural antibody against the donor will have disappeared, and the graft should be accepted by both the humoral and the cellular arms of the immune system. This approach has the added advantage of permitting organ transplantation to be performed sufficiently long following transplant of hematopoietic cells, e.g., BMT, e.g., a fetal liver suspension, that normal health and immunocompetence will have been restored at the time of organ transplantation. The use of xenogeneic donors allows the possibility of using bone marrow cells and organs from the same animal, or from genetically matched animals. As liver is the major site of hematopoiesis in the fetus, fetal liver can also serve as an alternative to bone marrow as a source of hematopoietic stem cells.

While any of these procedures may aid the survival of an implanted organ, best results are achieved when all steps are used in combination. Methods of the invention can be used to confer tolerance to allogeneic grafts, e.g., wherein both the graft donor and the recipient are humans, and to xenogeneic grafts, e.g., wherein the graft donor is a nonhuman animal, e.g., a swine, e.g., a miniature swine, and the graft recipient is a primate, e.g., a human.

In the case of xenogeneic grafts, the donor of the implant and the individual that supplies either the tolerance-inducing hematopoietic cells or the liver to be perfused should be the same individual or should be as closely related as possible. For example, it is preferable to derive implant tissue from a colony of donors that is highly or completely inbred.

Detailed Protocol

In the following protocol for preparing a cynomolgus monkey for receipt of a kidney from a miniature swine donor, zero time is defined as the moment that the arterial and venous cannulas of the recipient are connected to the liver to be perfused.

On day −1 a commercial preparation (Upjohn) of horse anti-human anti-thymocyte globulin (ATG) is injected into the recipient. ATG eliminates mature T cells and natural killer cells that would otherwise cause rejection of the bone marrow cells used to induce tolerance. The recipient is anesthetized, an IV catheter is inserted into the recipient, and 6 ml of heparinized whole blood are removed before injection. The ATG preparation is then injected (50 mg/kg) intravenously. Six ml samples of heparinized whole blood are dram for testing at time points of 30 min., 24 hrs and 48 hrs. Blood samples are analyzed for the effect of antibody treatment on natural killer cell activity (testing on K562 targets) and by FACS analysis for lymphocyte subpopulations, including CD4, CD8, CD3, CD11b, and CD16. Preliminary data from both assays indicate that both groups of cells are eliminated by the administration of ATG. If mature T cells and NK cells are not eliminated, ATG can be re- administered at later times in the procedure, both before and after organ transplantation.

Sublethal irradiation is administered to the recipient between days −1 and −8. Irradiation is necessary to eliminate enough of the recipient's endogenous BMC to stimulate hematopoiesis of the newly introduced foreign BMC. Sublethal total body irradiation is sufficient to permit engraftment with minimal toxic effects to the recipient. Whole body radiation (150 Rads) was administered to cynomolgus monkey recipients from a bilateral (TRBC) cobalt teletherapy Unit at 10 Rads/min. Local irradiation of the thymus (700 Rads) was also employed in order to facilitate engraftment.

Natural antibodies are a primary cause of organ rejection. To remove natural antibodies from the recipient's circulation prior to transplantation, on day 0 an operative absorption of natural antibodies (nAB) is performed, using a miniature swine liver, as follows. At −90 minutes the swine donor is anesthetized, and the liver prepared for removal by standard operative procedures. At −60 minutes the recipient monkey is anesthetized. A peripheral IV catheter is inserted, and a 6 ml sample of whole blood is dram. Through mid-line incision, the abdominal aorta and the vena cava are isolated. Silastic cannulas containing side ports for blood sampling are inserted into the blood vessels.

At −30 minutes the liver is perfused in situ until it turns pale, and then removed from the swine donor and placed into cold Ringers Lactate. The liver is kept cold until just prior to reperfusion in the monkey. A liver biopsy is taken. At −10 minutes the liver is perfused with warm albumin solution until the liver is warm (37 degrees).

At 0 time the arterial and venous cannulas of the recipient are connected to the portal vein and vena cava of the donor liver and perfusion is begun. Liver biopsies are taken at 30 minutes and 60 minutes, respectively. Samples of recipient blood are also drawn for serum at 30 minutes and 60 minutes respectively. At 60 minutes the liver is disconnected from the cannulas and the recipient's large blood vessels are repaired. The liver, having served its function of absorbing harmful natural antibodies from the recipient monkey, is discarded. Additional blood samples for serum are drawn from the recipient at 2, 24, and 48 hours. When this procedure was performed on two sequential perfusions of swine livers, the second liver showed no evidence of mild ischemic changes during perfusion. At the end of a 30 minute perfusion the second liver looked grossly normal and appeared to be functioning, as evidenced by a darkening of the venous outflow blood compared to the arterial inflow blood in the two adjacent cannulas. Tissue sections from the livers were normal, but immunofluorescent stains showed IgM on endothelial cells. Serum samples showed a decrease in natural antibodies.

To promote long-term survival of the implanted organ through T-cell and B-cell mediated tolerance, donor bone marrow cells are administered to the recipient to form chimeric bone marrow. The presence of donor antigens in the bone marrow allows newly developing B cells, and newly sensitized T cells, to recognize antigens of the donor as self, and thereby induces tolerance for the implanted organ from the donor. To stabilize the donor BMC, donor stromal tissue, in the form of tissue slices of fetal liver, thymus, and/or fetal spleen are transplanted under the kidney capsule of the recipient. Stromal tissue is preferably implanted simultaneously with, or prior to, administration of hematopoietic stem cells, e.g., BMC, or a fetal liver cell suspension.

To follow chimerism, two color flow cytometry can be used. This assay uses monoclonal antibodies to distinguish between donor class I major histocompatibility antigens and leukocyte common antigens versus recipient class I major histocompatibility antigens.

BMC can in turn be injected either simultaneously with, or preceding, organ transplant. Bone marrow is harvested and injected intravenously ($7.5 \times 10^8$/kg) as previously described (Pennington et al., 1988, *Transplantation* 45:21-26). Should natural antibodies be found to recur before tolerance is induced, and should these antibodies cause damage to the graft, the protocol can be modified to permit sufficient time following BMT for humoral tolerance to be established prior to organ grafting.

The approaches described above are designed to synergistically prevent the problem of transplant rejection. When a kidney is implanted into a cynomolgus monkey following liver absorption of natural antibodies, without use of bone marrow transplantation to induce tolerance, renal functions continued for 1-2 days before rejection of the kidney. When four steps of the procedure were performed (absorption of natural antibodies by liver perfusion, administration of ATG, sublethal irradiation and bone marrow infusion, followed by implant of a porcine kidney into a primate recipient), the kidney survived 7 days before rejection. Despite rejection of the transplanted organ, the recipient remained healthy.

When swine fetal liver and thymic stromal tissue were implanted under the kidney capsule of two sublethally irradiated SCID mice, 25–50% of peripheral blood leukocytes were of donor lineage two weeks post-transplantation. A significant degree of chimerism was not detected in a third animal receiving fetal liver without thymus. These procedures did not employ any chemical immunosuppressants.

Other Embodiments

Other embodiments are within the following claims.

For example, implanted grafts may consist of organs such as liver, kidney, heart; body parts such as bone or skeletal matrix; tissue such as skin, intestines, endocrine glands; or progenitor stem cells of various types.

The methods of the invention may be employed with other mammalian recipients (e.g., rhesus monkeys, humans) and may use other mammalian donors (e.g., primates, swine, sheep, dogs).

The methods of the invention may be employed in combination, as described, or in-part.

The method of introducing bone marrow cells may be altered, particularly by (1) increasing the time interval between injecting hematopoietic stem cells and implanting the graft; (2) increasing or decreasing the amount of hematopoietic stem cells injected; (3) varying the number of hematopoietic stem cell injections; (4) varying the method of delivery of hematopoietic stem cells; (5) varying the tissue source of hematopoietic stem cells, e.g., a fetal liver cell suspension may be used; or (6) varying the donor source of hematopoietic stem cells. Although hematopoietic stem cells derived from the graft donor are preferable, hematopoietic stem cells may be obtained from other individuals or species, or from genetically-engineered completely or partially inbred donor strains, or from in vitro cell culture.

Methods of preparing the recipient for transplant of hematopoietic stem cells may be varied. For instance, the recipient may undergo a splenectomy or a thymectomy. The latter would preferably by administered prior to the non-myeloablative regimen, e.g., at day −14.

Hemoperfusion of natural antibodies may: (1) make use of other vascular organs, e.g., liver, kidney, intestines; (2) make use of multiple sequential organs; (3) make use of varying the length of time each organ is perfused; (4) make use of varying the donor of the perfused organ. Irradiation of the recipient may make use of: (1) of varying the absorbed dose of whole body radiation below the sublethal range; (2) of targeting different body parts (e.g., thymus, spleen); (3) varying the rate of irradiation (e.g., 10 rads/min, 15 rads/min); or (4) varying the time interval between irradiation and transplant of hematopoietic stem cells; any time interval between 1 and 14 days can be used, and certain advantages may flow from use of a time interval of 4–7 days. Antibodies introduced prior to hematopoietic cell transplant may be varied by: (1) using monoclonal antibodies to T cell subsets or NK cells (e.g., anti-NKH$1_A$, as described by U.S. Pat. No. 4,772,552 to Hercend, et at., hereby incorporated by reference); (2) preparing anti-human ATG in other mammalian hosts (e.g., monkey, pig, rabbit, dog); or (3) using anti-monkey ATG prepared in any of the above mentioned hosts.

As an alternative or adjunct to hemoperfusion, host antibodies can be depleted by administration of an excess of hematopoietic cells.

Stromal tissue introduced prior to hematopoietic cell transplant, e.g., BMT, may be varied by: (1) administering the fetal liver and thymus tissue as a fluid cell suspension; (2) administering fetal liver or thymus stromal tissue but not both; (3) placing a stromal implant into other encapsulated, well-vascularized sites; or (4) using adult thymus or fetal spleen as a source of stromal tissue.

As is discussed herein, it is often desirable to expose a graft recipient to irradiation in order to promote the development of mixed chimerism. The inventor has discovered that it is possible to induce mixed chimerism with less radiation toxicity by fractionating the radiation dose, i.e., by delivering the radiation in two or more exposures or sessions. Accordingly, in any method of the invention calling for the irradiation of a recipient, e.g., a primate, e.g., a human, recipient, of a xenograft or allograft, the radiation can either be delivered in a single exposure, or more preferably, can be fractionated into two or more exposures or sessions. The sum of the fractionated dosages is preferably equal, e.g., in rads or Gy, to the radiation dosage which can result in mixed chimerism when given in a single exposure. The fractions are preferably approximately equal in dosage. For example, a single dose of 700 rads can be replaced with, e.g., two fractions of 350 rads, or seven fractions of 100 rads. Hyperfractionation of the radiation dose can also be used in methods of the invention. The fractions can be delivered on the same day, or can be separated by intervals of one, two, three, four, five, or more days. Whole body irradiation, thymic irradiation, or both, can be fractionated.

Methods of the invention can include recipient splenectomy.

As is discussed herein, hemoperfusion, e.g., hemoperfusion with a donor organ, can be used to deplete the host of natural antibodies. Other methods for depleting or otherwise inactivating natural antibodies can be used with any of the methods described herein. For example, drugs which deplete or inactivate natural antibodies, e.g., deoxyspergualin (DSG) (Bristol), or anti-IgM antibodies, can be administered to the recipient of an allograft or a xenograft. One or more of, DSG (or similar drugs), anti-IgM antibodies, and hemoperfusion, can be used to deplete or otherwise inactivate recipient natural antibodies in methods of the invention. DSG at a concentration of 6 mg/kg/day, i.v., has been found useful in suppressing natural antibody function in pig to cynomolgus kidney transplants.

Some of the methods described herein use irradiation to create hematopoietic space, and thereby prepare a recipient for the administration of allogeneic, xenogeneic, syngeneic, or genetically engineered autologous, stem cells. In any of the methods described herein, particularly primate or clinical methods, it is preferable to create hematopoietic space for the administration of such cells by non-lethal means, e.g., by administering sub-lethal doses of irradiation, bone marrow depleting drugs, or antibodies. The use of sublethal levels of bone marrow depletion allows the generation of mixed chimerism in the recipient. Mixed chimerism is generally preferable to total or lethal ablation of the recipient bone marrow followed by complete reconstitution of the recipient with administered stem cells.

Xenogeneic thymic tissue is easier to obtain and in general is less likely to harbor human pathogens. Thus, xenogeneic thymic tissue is preferred in methods for restoring or inducing immunocompetence. Allogeneic thymic tissue can however be used in these methods.

Some of the methods described herein include the administration of thymic irradiation, e.g., to inactivate host thymic-T cells or to otherwise diminish the host's thymic-T cell mediated responses to donor antigens. It has been discovered that the thymic irradiation called for in allogeneic or xenogeneic methods of the invention can be supplemented with, or replaced by, other treatments which diminish (e.g., by depleting thymic-T cells and/or down modulating one or more of the T cell receptor (TCR), CD4 co-receptor, or CD8 co-receptor) the host's thymus function, e.g., the host's thymic-T cell mediated response. For example, thymic irradiation can be supplemented with, or replaced by, anti-T cell antibodies (e.g., anti-CD4 and/or anti-CD8 monoclonal antibodies) administered a sufficient number of times, in sufficient dosage, for a sufficient period of time, to diminish the host's thymic-T cell mediated response.

For best results, anti-T cell antibodies should be administered repeatedly. E.g., anti-T cell antibodies can be administered one, two, three, or more times prior to donor thymus or bone marrow transplantation. Typically, a pre-thymus or bone marrow transplantation dose of antibodies will be given to the patient about 5 days prior to thymus or bone marrow transplantation. Additional, earlier doses 6, 7, or 8 days prior to thymus or bone marrow transplantation can also be given. It may be desirable to administer a first treatment then to repeat pre-thymus or bone marrow administrations every 1–5 days until the patient shows excess antibodies in the serum and about 99% depletion of peripheral T cells and then to perform the bone marrow transplantation. Anti-T cell antibodies can also be administered one, two, three, or more times after thymus or donor bone marrow transplantation. Typically, a post-thymus or bone marrow transplant treatment will be given about 2–14 days after bone marrow transplantation. The post thymus or bone marrow administration can be repeated as many times as needed. If more than one administration is given the administrations can be spaced about 1 week apart. Additional doses can be given if the patient appears to undergo early or unwanted T cell recovery. Preferably, anti-T cell antibodies are administered at least once (and preferably two, three, or more times) prior to donor thymus or bone marrow transplantation and at least once (and preferably two, three, or more times) after donor thymus or bone marrow transplantation.

It has also been discovered that much or all of the preparative regimen, if called for, can be delivered or administered to a recipient, e.g., an allograft or xenograft recipient, within a few days, preferably within 72, 48, or 24 hours, of transplantation of tolerizing stem cells and/or the graft. This is particularly useful in the case of humans receiving grafts from cadavers. Accordingly, in any oft he methods of the invention calling for the administration of treatments prior to the transplant of stem cells and/or a graft, e.g., treatments to inactivate or deplete host antibodies, treatments to inactivate host T cells or NK cells, or irradiation, the treatment(s) can be administered, within a few days, preferably within 72, 48, or 24 hours, of transplantation of the stem cells and/or the graft. In particular, primate, e.g., human, recipients of allografts can be given any or all of treatments to inactivate or deplete host antibodies, treatments to inactivate host T cells or NK cells, or irradiation, within a few days, preferably within 72, 48, or 24 hours, of transplantation of stem cells and/or the graft. For example, treatment to deplete recipient T cells and/or NK cells, e.g., administration of ATG, can be given on day −2, −1, and 0, and WBI, thymic irradiation, and stem cell, e.g., bone marrow stem cells, administered on day 0. (The graft, e.g., a renal allograft, is transplanted on day 0).

As described in PCT/US94/01616, hereby incorporated by reference, it has been discovered that there is a permissible time period ("window") for hematopoietic stem cell engraftment following the creation of space (e.g., by whole body irradiation) for the donor hematopoietic stem cells in a recipient. It has further been discovered that space created for hematopoietic stem cell engraftment can be monitored over time by monitoring peripheral white blood cell levels in a recipient. The myelosuppressive treatment sufficient to create hematopoietic space generally results in a reduction in white blood cell (WBC) levels (as revealed, e.g., by WBC counts) and the WBC reduction serves as a marker for the presence of hematopoietic space. The marker is a conservative one since WBC counts may recover at a time when space is still present in an animal.

Accordingly, in any method which involves hematopoietic stem cell transplantation, and thus also requires the creation of hematopoietic space in a recipient, transplantation can be performed during the permissible window for engraftment following creation of space for the hematopoietic stem cells. Likewise, in any method in which space is created for exogenously administered hematopoietic stem cells, white blood cell levels can be followed to monitor space for the donor hematopoietic stem cells (i.e., to assess the permissible window for engraftment). Examples of procedures involving hematopoietic stem cell transplantation include: 1) conditioning of a recipient for an allo- or xenograft in which hematopoietic stem cell transplantation is performed in conjunction with transplantation of another allo- or xenograft; 2) treatment of various hematopoietic disorders, including Leukemias, lymphomas and other hematopoietic malignancies and genetic hematopoietic disorders (e.g., adenosine deaminase deficiency, bare lymphocyte syndrome and other congenital immunodeficiency diseases) in which hematopoietic stem cell transplantation is performed therapeutically; and 3) transplantation of genetically modified hematopoietic stem cells (e.g., genetically modified autologous hematopoietic stem cells) to deliver a gene product to a recipient (e.g., as gene therapy).

Accordingly, methods of the invention include a method of determining if a myelosuppressive or hematopoietic-space inducing treatment is sufficient to create hematopoietic space. The method includes administering a myelosuppressive treatment to a recipient, and determining the level of white blood cells in the recipient, e.g., by determining the WBC count of the recipient, a depression in the level of white blood cells being indicative of the presence or induction of hematopoietic space.

As is discussed in PCT/US94/01616, hereby incorporated by reference, and elsewhere herein, the engraftment of exogenously supplied hematopoietic stem cells can be promoted by treating the recipient of the cells so as to induce hematopoietic space in the recipient. Hematopoietic space is commonly induced by radiation, but other procedures can replace or reduce the need for WBI. For example, space can be created by treating the recipient with a monoclonal antibody against MHC class I antigens expressed by the recipient (see e.g., Voralia, M. et al. (1987) Transplantation 44:487) or space can be created by treating the recipient with myelosuppressive drugs (see e.g., Lapidot, T. et al. (1990) Proc. Natl. Acad. Sci. USA 87:4595).

It has also been found that the direct introduction of donor antigen, e.g., donor hematopoietic stem cells, into the thymus of a recipient, can modify the immune response of the recipient. Thus, embodiments oft he invention include methods of promoting the acceptance a graft (e.g., by prolonging the acceptance the graft) by a recipient, by introducing into the recipient, donor antigen. The graft can be an allo graft, e.g., a graft from a primate e.g., a human, which is introduced into a primate of the same species. The graft can be a concordant or discordant xenograft. E.g., the graft can be a miniature swine graft introduced into a second species, e.g., a primate, e.g., a human.

What is claimed is:

1. A method of restoring or promoting the thymus-dependent ability for T cell progenitors to develop into mature functional T cells in a primate recipient which is capable of producing T cell progenitors but which is thymus-function deficient comprising, inactivating mature T cells of said recipient, swine xenogeneic fetal or neonatal thymus so that recipient T cells can mature in said implanted swine xenogeneic thymus tissue.

2. The method of claim 1, further comprising implanting swine fetal liver tissue in said recipient.

3. The method of claim 1, wherein said primate recipient is a human and said donor is a swine.

4. The method of claim 1, wherein said primate recipient is a human and said donor is a miniature swine.

5. The method of claim 1, wherein said swine thymic graft is capable of supporting clonal deletion or energy or thymocytes reactive with donor xenoantigens.

6. The method of claim 1, further comprising introducing swine hematopoietic cells into said receipent and inactivating NK cells of said recipient.

7. A method of inducing tolerance in a receipent primate of a first species to a graft obtained from a swine, said method comprising prior or simultaneous with transplantation of said graft, introducing into said recipient, swine thymic tissue, inactivating mature T cells of said recipient, and implanting said graft in said recipient, wherein said swine thymic graft supports maturation of recipient T cells.

8. The method of claim 7, wherein the same swine is the donor of both the graft and the thymic tissue.

9. The method of claim 7, wherein said primate is a human.

10. The method of claim 7, further comprising the step of prior to thymic tissue transplantation, irradiating the recipient with low dose whole body irradiation.

11. The method of claim 10, wherein said low dose irradiation is at least 100 rads and less than 400 rads.

12. The method of claim 7, further comprising the step prior to thymic tissue transplantation, absorbing natural antibodies from the blood of said recipient.

13. The method of claim 7, wherein said swine thymic graft is capable of supporting clonal deletion or energy of thymocytes reactive with donor xenoantigens.

14. The method of claim 7, wherein said swine thymic graft is fetal or neonatal.

15. The method of claim 7, wherein hematopoietic cells are administered to said recipient and wherein the method includes inactivating NK cells of said recipient.

16. The method of claim 7, wherein said primate recipient is a human and said donor is a miniature swine.

17. A method of providing mature recipient T cells in a primate recipient which is thymus function deficient, comprising introducing into the primate recipient, swine xenogeneic donor thymic tissue, so that recipient T cells can mature in said implanted swine donor thymic tissue.

18. The method of claim 2, wherein said primate is a human and said donor is a swine.

19. The method of claim 7, wherein said primate is a human and said donor is a miniature swine.

20. The method of claim 17, wherein said thymus function is deficient in said recipient due to an immune disorder.

21. A method of providing mature swine donor T cells to a primate recipient which is unable to produce a normal number of mature T cells, comprising inactivating mature T cells of the recipient;

inactivating NK cells of the receipent; and introducing into said primate recipient, a composition comprising swine xenogeneic donor hematopoietic stem cells, so that said swine donor T cells can mature in the recipient thymus.

22. The method of claim 21, wherein said primate is a human and said donor is a miniature swine.

23. The method of claim 21, wherein said primate is a human.

24. The method of claim 21, wherein said thymus function is deficient in said recipient due to an immune disorder.

* * * * *

UNITED STATES PATENT AND TRADEMARK OFFICE
CERTIFICATE OF CORRECTION

PATENT NO. : 5,658,564

DATED : August 19, 1997

INVENTOR(S) : Megan Sykes, and David Sachs

It is certified that error appears in the above-identified patent and that said Letters Patent is hereby corrected as shown below:

Col. 1, line 34, "gaff" should be --graft--.

Col. 1, line 36-37, "immunoincompetent" should be --immunocompetent--.

Col. 2, line 38, "drag" should be --drug--.

Col. 2, line 40, "absorption" should be --adsorption--.

Col. 4, line 51, "drag" should be --drug--.

Col. 4, line 53, "an anti-IgM antibodies" should be -an anti-IgM antibody--.

Col. 4, line 53, "absorption" should be --adsorption--.

Col. 6, line 35, "an anti-IgM antibodies" should be -an anti-IgM antibody--.

Col. 6, line 35, "absorption" should be --adsorption--.

Col. 8, line 23, "an anti-IgM antibodies" should be -an anti-IgM antibody--.

Col. 8, line 23, "absorption" should be --adsorption--.

Col. 10, line 30, "an anti-IgM antibodies" should be -an anti-IgM antibody--.

Col. 10, line 30, "absorption" should be --adsorption--.

Col. 12, line 29, "an anti-IgM antibodies" should be -an anti-IgM antibody--.

UNITED STATES PATENT AND TRADEMARK OFFICE
CERTIFICATE OF CORRECTION

PATENT NO. : 5,658,564
DATED : August 19, 1997
INVENTOR(S) : Megan Sykes and David H. Sachs It is certified that error appears in the above-identified patent and that said Letters Patent is hereby corrected as shown below:

Col. 12, line 29, "absorption" should be --adsorption--.

Col. 13, line 59, "an anti-IgM antibodies" should be -an anti-IgM antibody--.

Col. 13, line 59, "absorption" should be --adsorption--.

Col. 14, line 43, "tetnus" should be --tetanus--.

Col. 16, line 5, "carded" should be --carried--.

Col. 16, line 43, "absorbed" should be --adsorbed--.

Col. 16, line 48, "absorb" should be --adsorb--.

Col. 16, line 58, "absorber" should be --adsorber--.

Col. 17, line 18, "regime" should be --regimen--.

Col. 17, line 37, "thymospoiesis" should be --thymopoiesis--.

Col. 17, line 40, "(FMC)" should be --(FCM)--.

Col. 17, line 47, "Loost-tx" should be -post-tx--.

Col. 17, line 49, "TRC$^{hi}$" should be --TCR$^{hi}$--.

Col. 17, line 60, " TCT$^{hi}$ " should be --TCR$^{hi}$--.

Col. 18, line 9, "I-e" should be --I-E--.

Col. 18, line 23, "cotrico" should be --cortico--.

UNITED STATES PATENT AND TRADEMARK OFFICE
CERTIFICATE OF CORRECTION

PATENT NO. : 5,658,564
DATED : August 19, 1997
INVENTOR(S) : Megan Sykes, and David Sachs Page 3 of 5

It is certified that error appears in the above-identified patent and that said Letters Patent is hereby corrected as shown below:

Col. 18, line 29, "hornology" should be --homology--.

Col. 18, line 41, "Clona" should be --Clonal--.

Col. 18, line 47, "Asiao" should be --Asialo--.

Col. 19, line 27, "regime" should be --regimen--.

Col. 19, line 39, "denaritic" should be --dendritic--.

Col. 20, line 7, "Or" should be --or--.

Col. 20, line 14, "post-Ix" should be -post-tx--.

Col. 20, line 26, "post-Ix" should be --post-tx--.

Col. 20, line 31, "αβTRC" should be --αβTCR--.

Col. 20, line 42, "post-Ix" should be --post-tx--.

Col. 21, line 4, "pyrovale" should be --pyruvate--.

Col. 21, line 5, "penlcillin" should be --penicillin--.

Col. 21, line 13, "Tomtee" should be --Tomtec--.

Col. 22, line 41, "CDS" should be --CD8--.

Col. 23, line 33, "thymo cyte" should be --thymocyte--.

Col. 23, line 51, "immuno competence" should be --immunocompetence--.

Col. 24, line 17, "absorbed" should be --adsorbed--.

UNITED STATES PATENT AND TRADEMARK OFFICE
CERTIFICATE OF CORRECTION

PATENT NO. : 5,658,564
DATED : August 19, 1997
INVENTOR(S) : Megan Sykes, and David Sachs It is certified that error appears in the above-identified patent and that said Letters Patent is hereby corrected as shown below:

Col. 24, line 44, "flee" should be --free--.

Col. 25, line 37, "mi" should be --ml--.

Col. 25, line 40, "dram" should be --drawn--.

Col. 25, line 48, "re- administer" should be --re-administer--.

Col. 25, line 62, "absorption" should be --adsorption--.

Col. 26, line 1, "dram" should be --drawn--.

Col. 26, line 63, "absorption" should be --adsorption--.

Col. 26, line 66, "absorption" should be --adsorption--.

Col. 27, line 49, "absorbed" should be --adsorbed--.

Col. 29, line 50, "oft he" should be --of the--.

Col. 30, line 1, "PCTFUS94/01616" should be -PCTUS94/01616--.

Col. 31, line 1, "allo graft" should be --allograft--.

Col. 31, line 13 (claim 1), please insert the phrase --introducing into said primate recipient-- in front of the word "swine"

Col. 31, line 24 (claim 5), "energy" should be --anergy--.

Col. 31, line 27 (claim 6), "receipent" should be --recipient--.

UNITED STATES PATENT AND TRADEMARK OFFICE
CERTIFICATE OF CORRECTION

PATENT NO. : 5,658,564

DATED : August 19, 1997

INVENTOR(S) : Megan Sykes, and David Sachs

It is certified that error appears in the above-identified patent and that said Letters Patent is hereby corrected as shown below:

Col. 31, line 29 (claim 7), "receipent" should be --recipient--.

Col. 32, line 4, "absorbing" should be --adsorbing--.

Col. 32, line 7, "energy" should be --anergy--.

Signed and Sealed this

Twenty-second Day of June, 1999

Attest:

Q. TODD DICKINSON

*Attesting Officer*   *Acting Commissioner of Patents and Trademarks*